(12) United States Patent
Hayakawa et al.

(10) Patent No.: US 10,569,066 B2
(45) Date of Patent: Feb. 25, 2020

(54) MEDICAL DEVICE

(71) Applicant: TERUMO KABUSHIKI KAISHA, Shibuya-ku, Tokyo (JP)

(72) Inventors: Koichi Hayakawa, Tokyo (JP); Yuri Akimoto, Hadano (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 1157 days.

(21) Appl. No.: 14/872,860

(22) Filed: Oct. 1, 2015

(65) Prior Publication Data
US 2016/0095602 A1    Apr. 7, 2016

(30) Foreign Application Priority Data

Oct. 3, 2014 (JP) .................................. 2014-205133

(51) Int. Cl.
| | |
|---|---|
| A61M 29/00 | (2006.01) |
| A61B 17/12 | (2006.01) |
| A61M 25/00 | (2006.01) |
| A61B 17/00 | (2006.01) |
| A61M 25/10 | (2013.01) |

(52) U.S. Cl.
CPC ....... *A61M 29/00* (2013.01); *A61B 17/12109* (2013.01); *A61B 17/12186* (2013.01); *A61M 25/0074* (2013.01); *A61B 17/00491* (2013.01); *A61B 17/12031* (2013.01);
(Continued)

(58) Field of Classification Search
CPC .... A61B 17/320725; A61B 17/320758; A61B 17/32056; A61B 17/3207; A61B 17/32075; A61B 17/12031; A61B 17/12109; A61B 17/12186; A61B 17/12131; A61B 17/1214; A61B 17/12145; A61B 17/1215;
(Continued)

(56) References Cited

U.S. PATENT DOCUMENTS

| | | | | |
|---|---|---|---|---|
| 3,205,863 A | * | 9/1965 | Rhoades | B43K 24/084 401/111 |
| 6,409,739 B1 | * | 6/2002 | Nobles | A61B 17/11 606/148 |

(Continued)

FOREIGN PATENT DOCUMENTS

JP    H-11-262527    9/1999

*Primary Examiner* — Diane D Yabut
(74) *Attorney, Agent, or Firm* — Buchanan Ingersoll & Rooney PC

(57) ABSTRACT

A medical device and treatment method for treating veins. The medical device includes: an elongated outer sheath; an inner member extending through inside of the outer sheath, the inner member protruding distally beyond the outer sheath; an expansion portion positioned between a distal portion of the outer sheath and a distal portion of the inner member, the expansion portion having a plurality of linear material portions extending along an axial direction of the inner member, the expansion portion being expandable in a radial direction of the inner member; a biasing member disposed inside the outer sheath biasing the inner member proximally relative to the outer sheath; and a fixing portion configured to fix the relative positions of the inner member and the outer sheath in a state in which the expansion portion has been expanded. The fixing portion is also configured to be released from the fixed state.

12 Claims, 18 Drawing Sheets

(52) U.S. Cl.
CPC .............. *A61B 2017/00986* (2013.01); *A61B 2017/1205* (2013.01); *A61M 2025/1052* (2013.01)

(58) Field of Classification Search
CPC ... A61B 17/12154; A61B 2017/00986; A61M 2025/1052; A61M 25/0074; A61M 29/00
See application file for complete search history.

(56) References Cited

U.S. PATENT DOCUMENTS

| | | |
|---|---|---|
| 7,077,836 B2 | 7/2006 | Lary et al. |
| 7,597,703 B2 * | 10/2009 | Sater ................ A61B 17/12022 606/198 |
| 7,862,575 B2 | 1/2011 | Tal |
| 2002/0010418 A1 | 1/2002 | Lary et al. |
| 2013/0274711 A1 * | 10/2013 | O'Day .............. A61M 5/16813 604/508 |

* cited by examiner

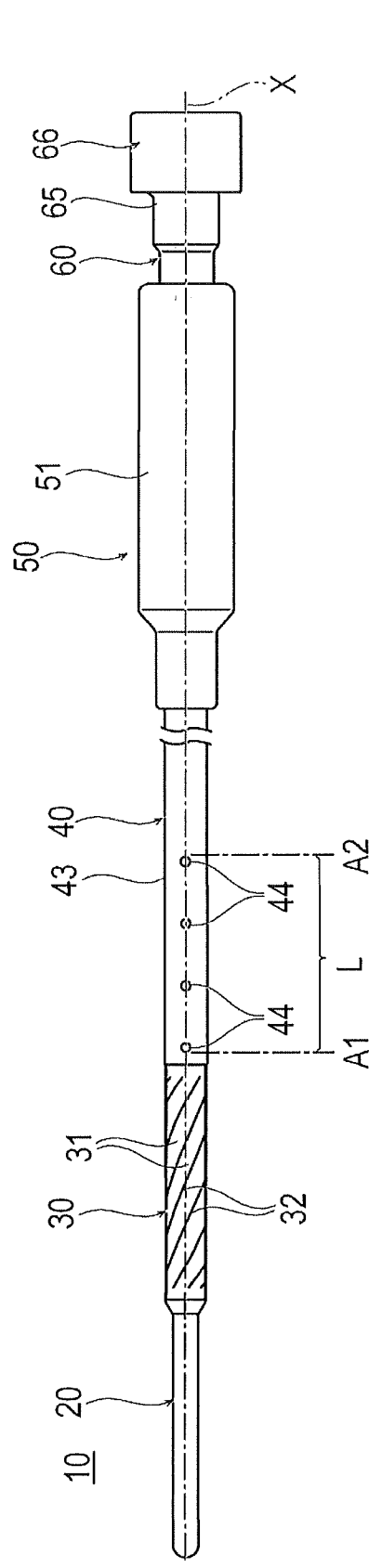
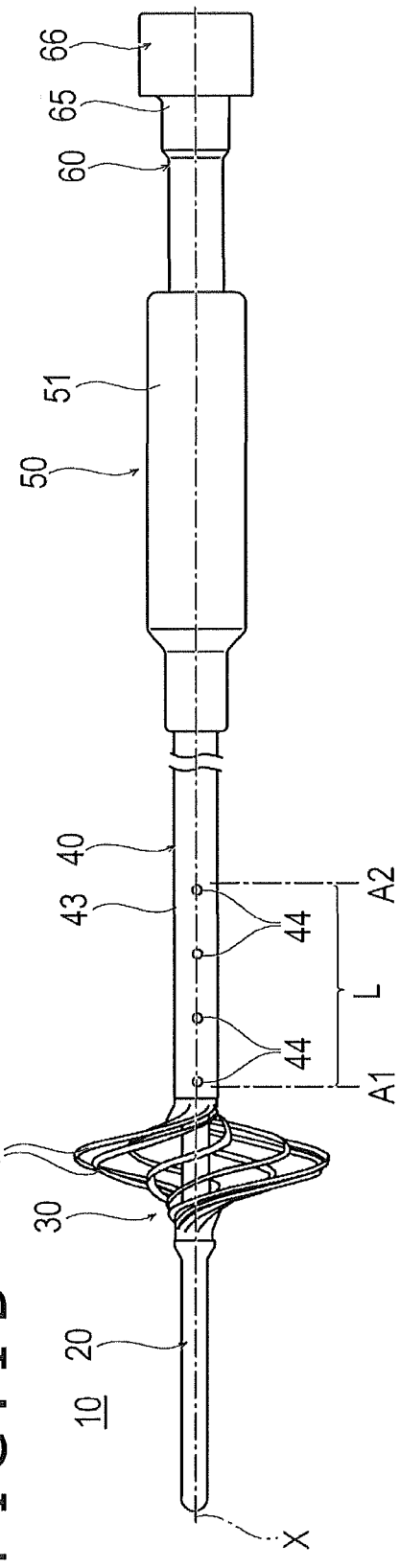
FIG. 1A
FIG. 1B

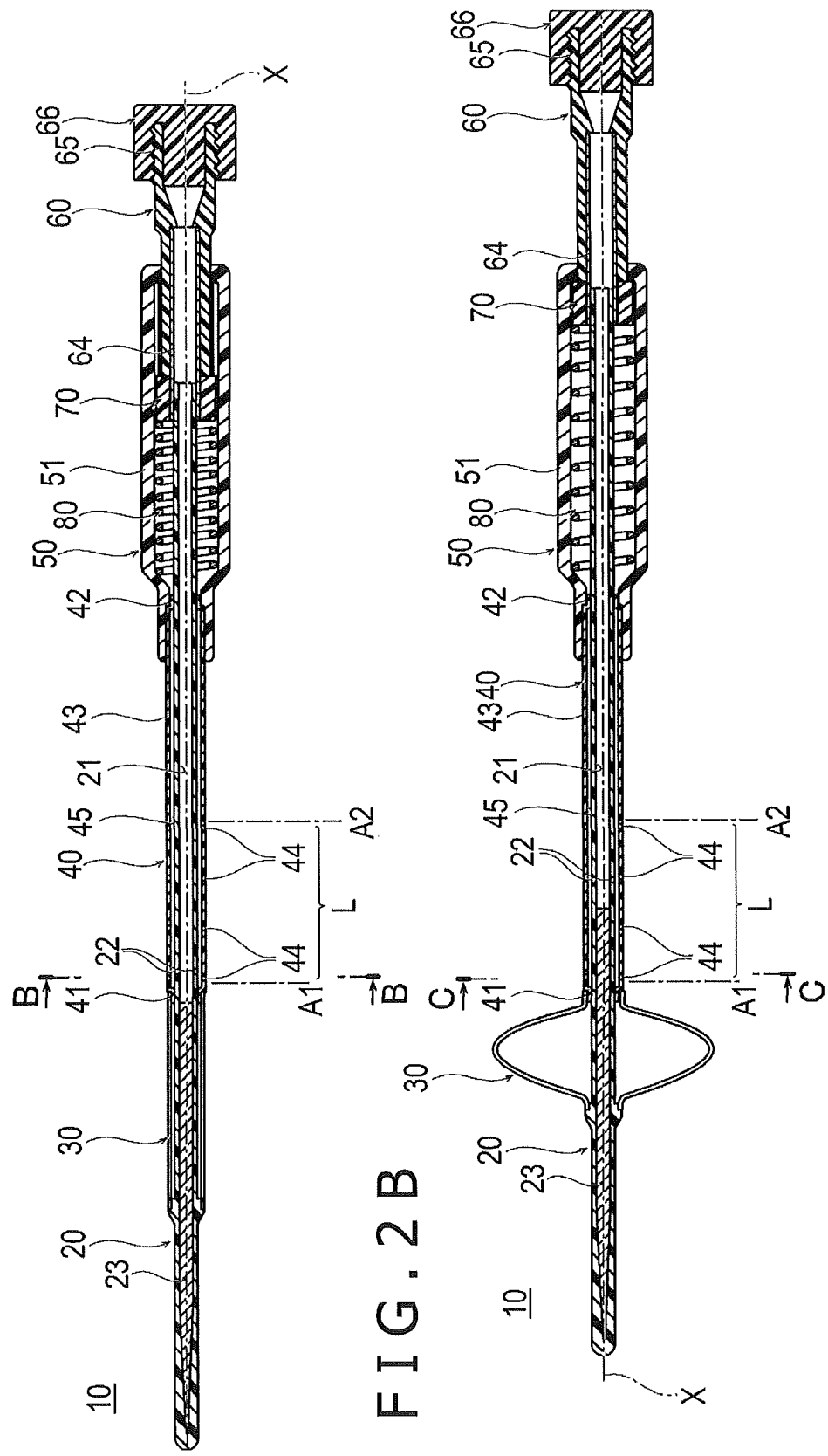

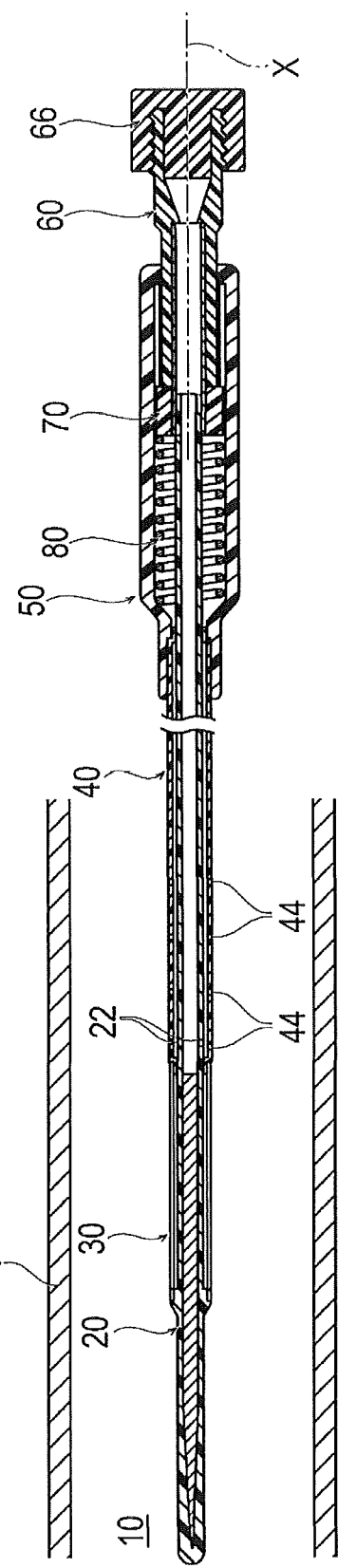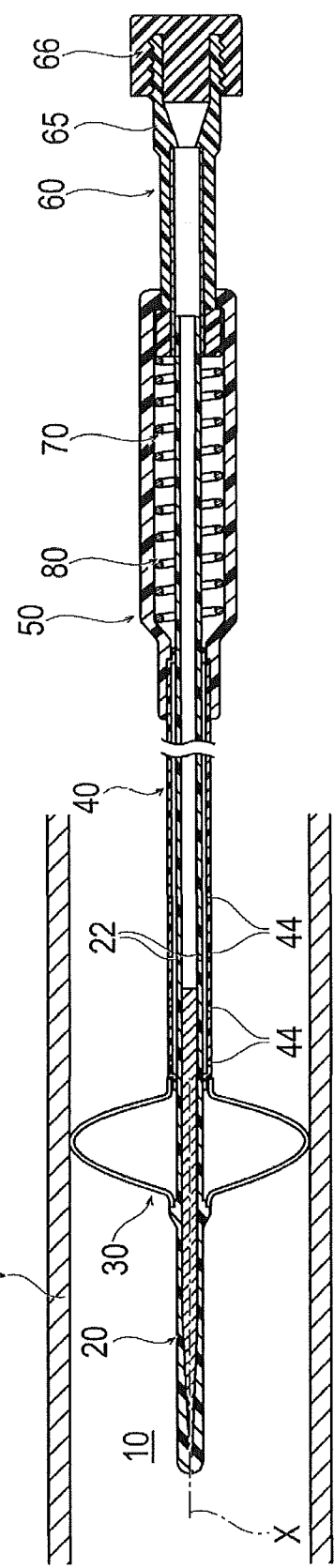

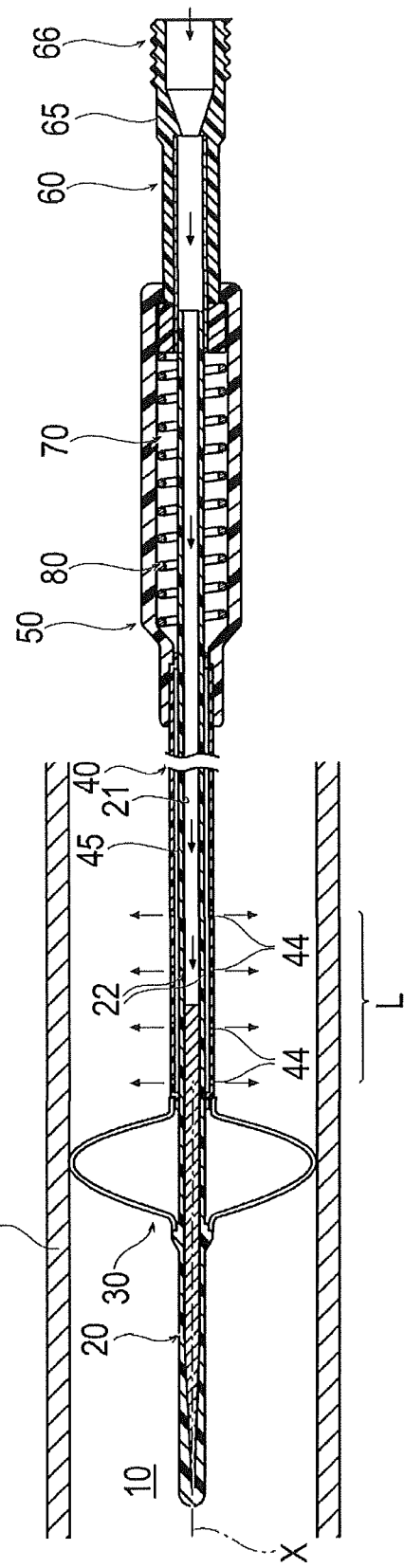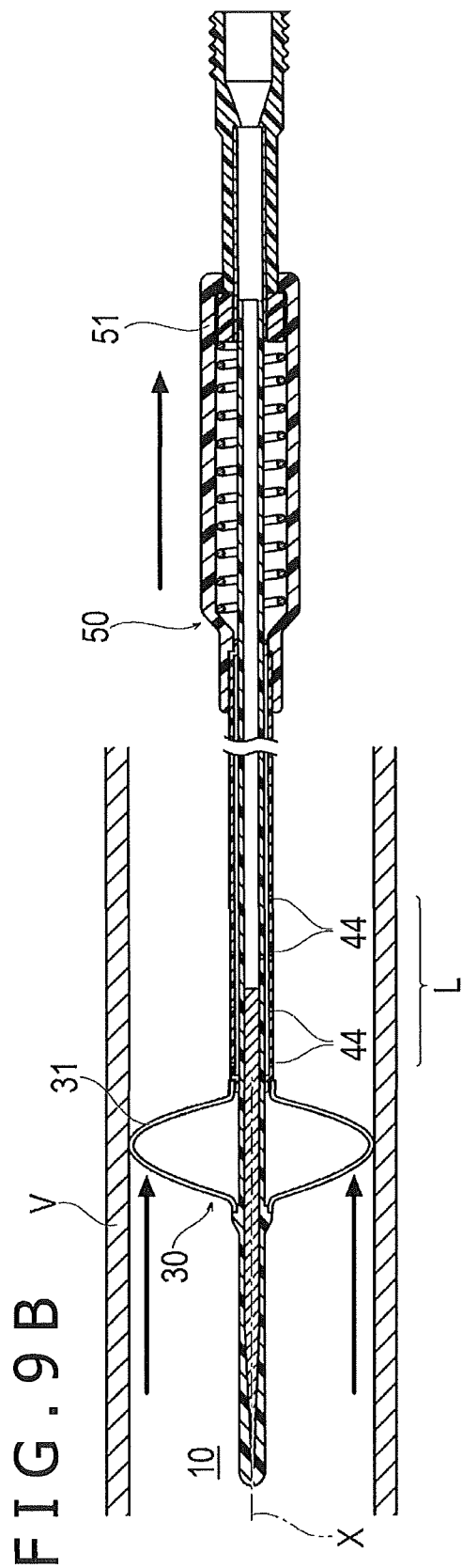

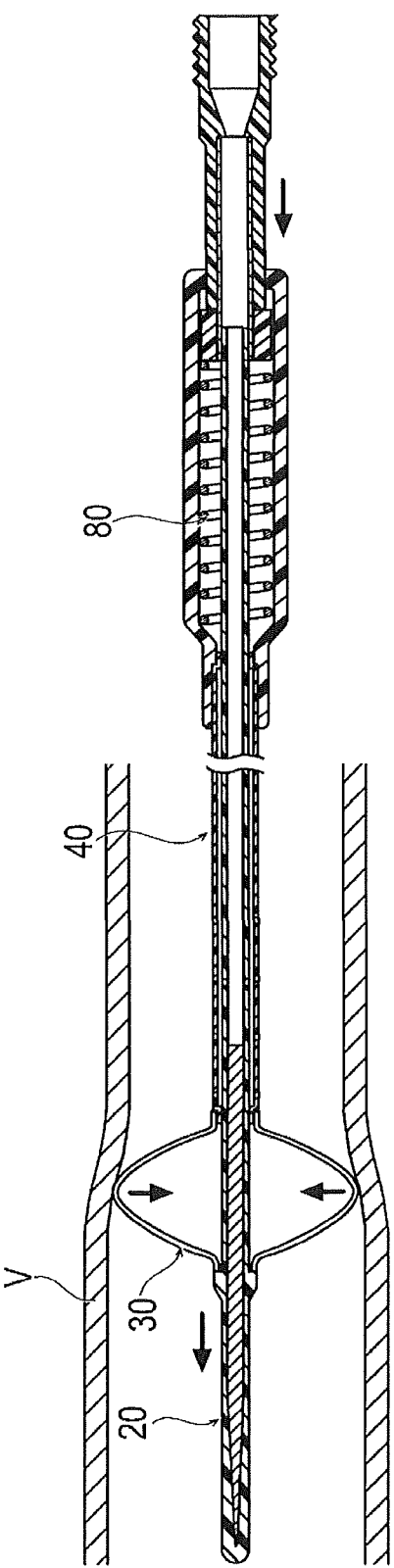

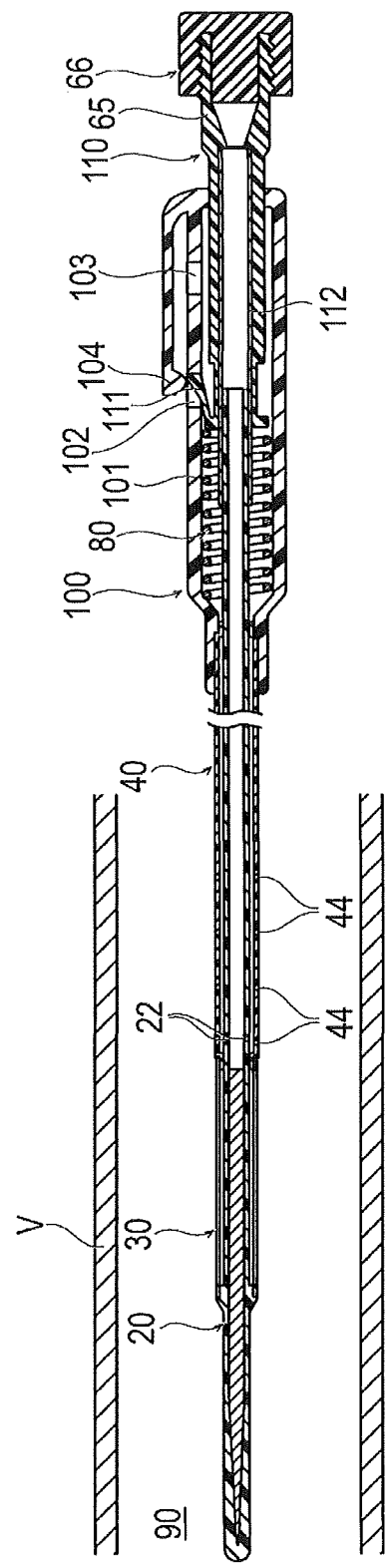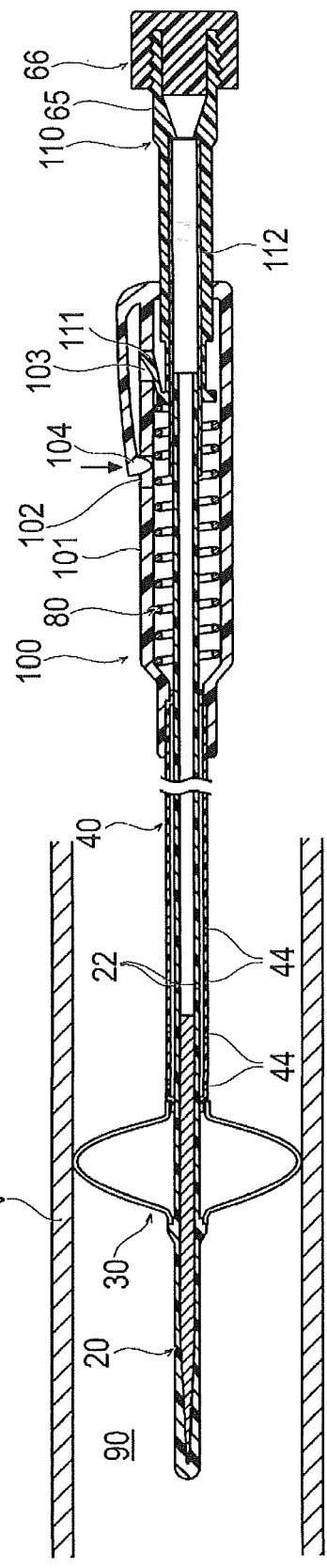

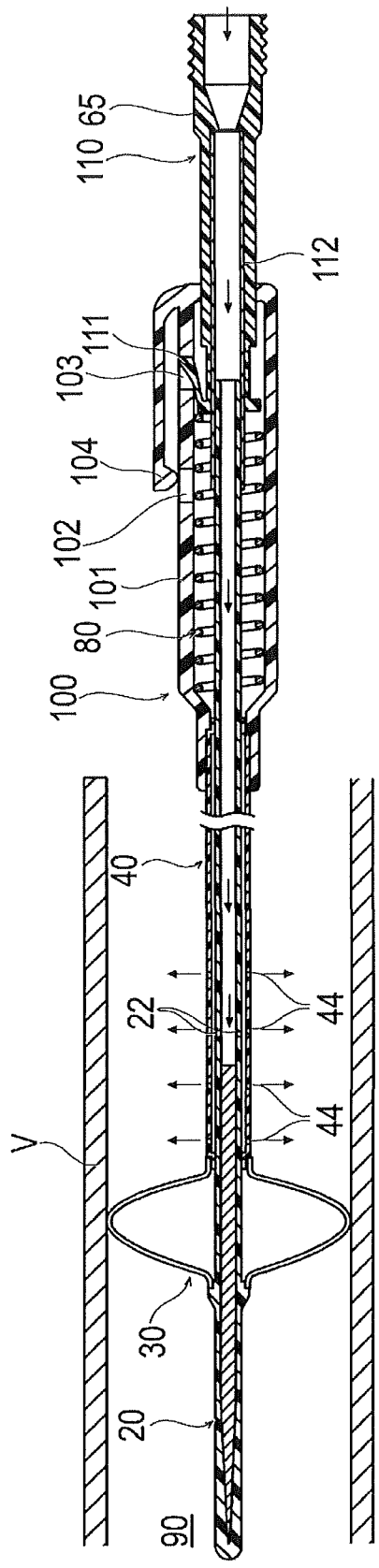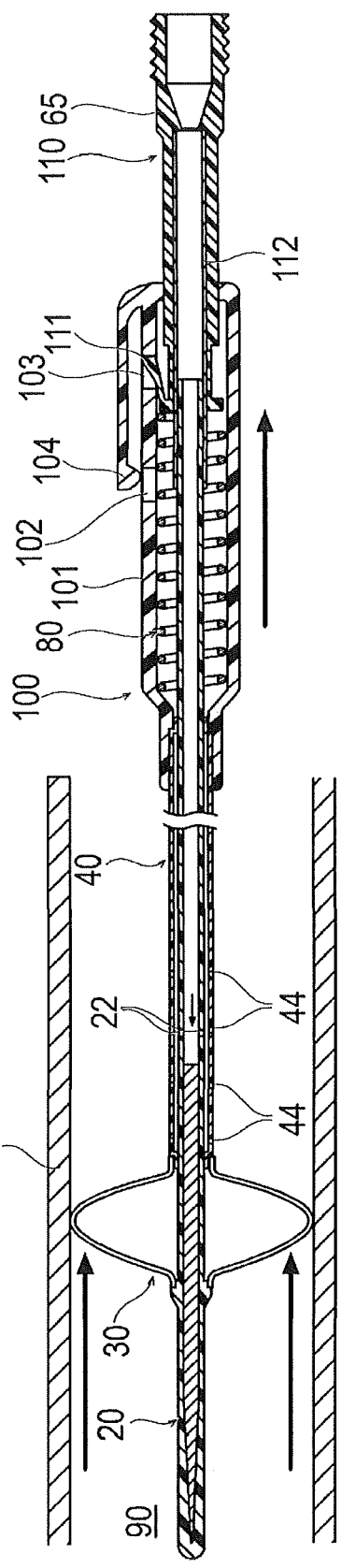

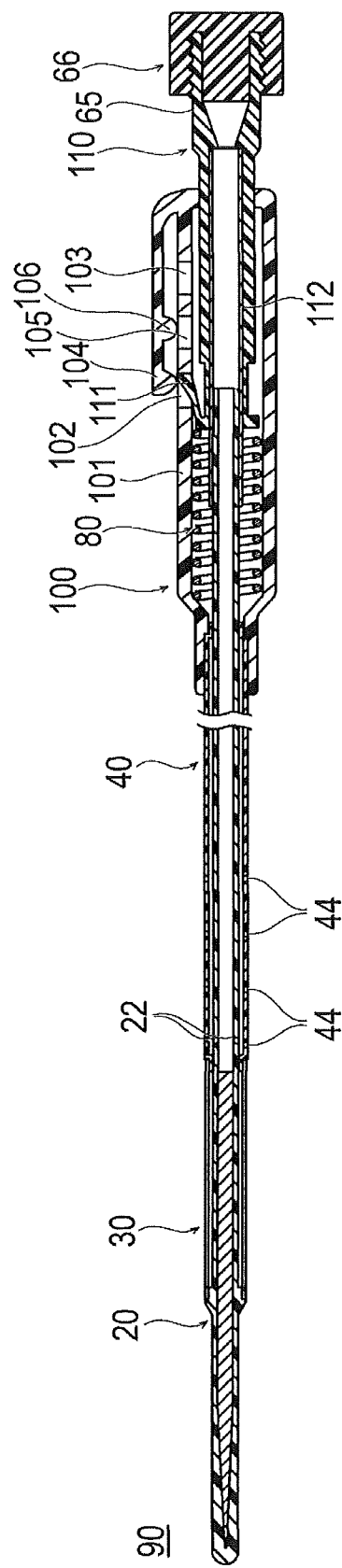

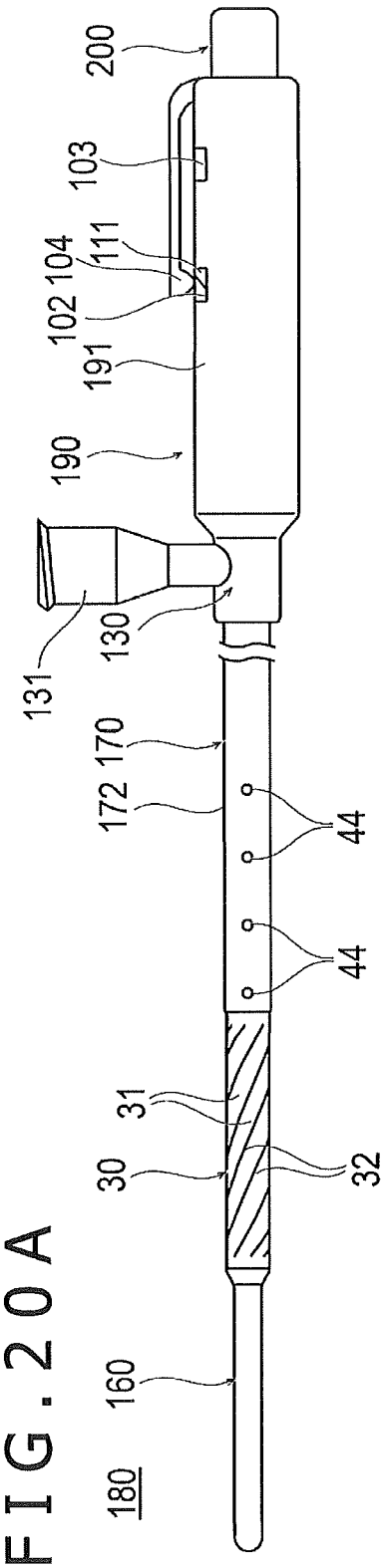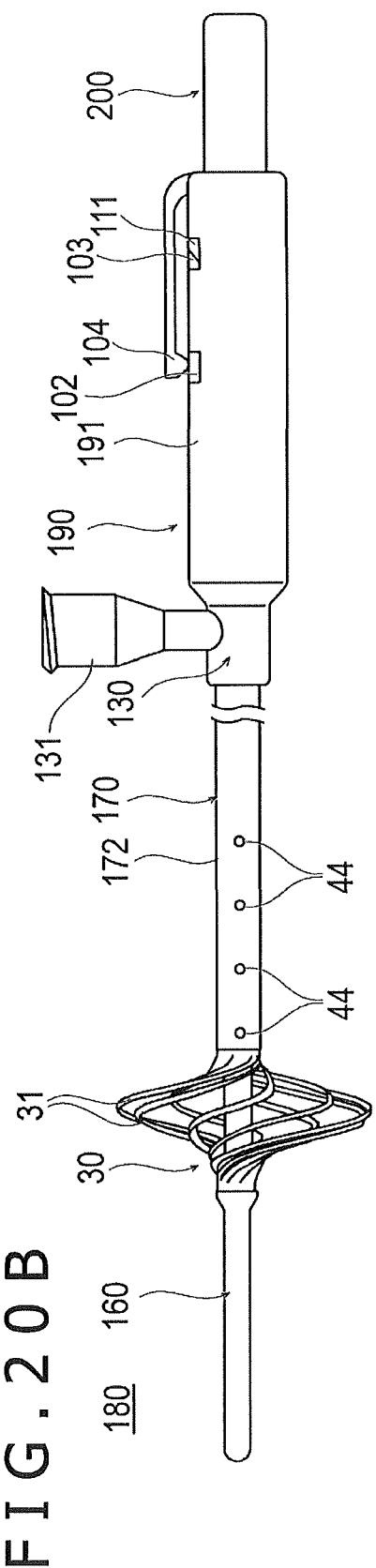

MEDICAL DEVICE

CROSS-REFERENCES TO RELATED APPLICATIONS

This application is a continuation of International Application No. PCT/JP2014/205133 filed on Oct. 3, 2014, the entire content of which is incorporated herein by reference.

TECHNICAL FIELD

The present disclosure relates to a medical device for treating a vein. More particularly, the disclosure relates to a device for occluding or contracting a varicose vein.

Veins are provided with venous valves to prevent the backflow of blood. Venous valves in the lower limb are contracted by muscles of the lower limb, so as to also function as a pump for returning blood to the heart against the effect of gravity.

When a venous valve becomes unable to operate normally, backflow of blood occurs in the vein and the vein enlarges, which may cause a varicose vein. Varicose veins often occur in the great saphenous vein and the small saphenous vein, which are superficial veins in the lower limb that are subject to relatively high pressures when the body is in a standing position. If a venous valve in the superficial vein stops operating normally, the blood which normally flows from the superficial vein into a deep vein instead flows from the deep vein into the superficial vein. This reverse flow may enlarge the superficial vein, causing a tortuous varicose vein.

Methods of treating varicose veins in the lower limb include a method of removing the vein itself (i.e., stripping) and a method of occluding the vein. Examples of the method of occluding the vein include a therapy by compressing the vein from the outside, a high ligation method in which the vein suffering from the varicose vein is ligated at a high position to prevent backflow of blood, an ablation therapy in which the vein is occluded by thermal cauterization using RF (radiofrequency wave) or laser, a therapy in which the varicose vein is occluded by use of a sclerosant, and a therapy in which the inner wall of the varicose vein is stimulated to occlude the blood vessel.

For example, U.S. Pat. No. 7,077,836 describes a device for occluding a varicose vein, wherein a self-expanding balloon (expansion portion) is expanded within the varicose vein and moved to stimulate and damage the inner wall of the varicose vein, attended further by injection of a sclerosant.

The device described in U.S. Pat. No. 7,077,836, however, has drawbacks as follows. At the time of expanding the expansion portion for damaging the inner wall of the varicose vein or at the time of contracting the expansion portion, the inner tube and the outer tube, which are connected to the expansion portion, may be operated to move relative to each other. This operation is intricate to carry out and makes it difficult to perform other operations.

SUMMARY

The medical device disclosed here enables an expansion portion to be expanded and contracted from a suitable state by only simple operations.

In one aspect, a medical device includes: an elongated outer sheath; an inner member extending through inside of the outer sheath, the inner member protruding distally beyond the outer sheath; an expansion portion positioned between a distal portion of the outer sheath and a distal portion of the inner member, the expansion portion having a plurality of linear material portions extending along an axial direction of the inner member, the expansion portion being expandable while bending in a radial direction of the inner member by moving the inner member proximally relative to the outer sheath; a biasing member disposed inside the outer sheath, the biasing member biasing the inner member proximally relative to the outer sheath; a fixing portion capable of fixing positions of the inner member and the outer sheath in a state in which the expansion portion has been expanded by moving the inner member proximally relative to the outer sheath while compressing the biasing member; and a releasing portion enabling the fixed state at the fixing portion to be released by distal pressing of the releasing portion.

Another aspect of the disclosure here involves a medical device including an elongated outer sheath possessing a distal end and an inner member inside the outer sheath, the inner member possessing a distal end positioned distally of the distal end of the outer sheath, and the inner member being axially movable in an axial direction relative to the outer sheath. The medical device further includes an expansion portion between the distal end of the outer sheath and the distal end of the inner member, the expansion portion comprising a plurality of linear material portions, the expansion portion being movable between a non-expanded position in which the linear material portions extend in the axial direction and an expanded position in which the linear material portions expand radially outwardly by virtue of the inner member moving proximally in a proximal direction relative to the outer sheath. The medical device also includes a rotatable member rotatably positioned inside the outer sheath, a body connected to the outer sheath, and a biasing member inside the outer sheath, the biasing member applying a biasing force to the rotatable member in the proximal direction so that the rotatable member is a spring-biased rotatable member. The rotatable member is rotatable inside the outer sheath between a first position in which the body prevents the biasing force from axially moving the inner member in the proximal direction, whereby the expansion portion remains in the non-expanded position, and a second position in which the spring-biased rotatable member applies the biasing force to the inner member to automatically axially move the inner member relative to the outer sheath in the proximal direction, whereby the expansion portion expands to the expanded position. The inner member and the outer sheath are relatively axially movable so that the inner member moves in a distal direction to cause a part movable with the inner member to contact the rotatable member so that the rotatable member shifts from the first position to the second position, whereupon the biasing force of the biasing member is applied to the inner member to axially move the inner member in the proximal direction.

The medical device configured as above enables the expansion portion to be easily maintained in a predetermined-sized state by the fixing portion. In addition, the fixed state can be released by pushing only the releasing portion. Therefore, the expansion portion can easily be expanded to and contracted from a suitable state by only simple operations.

Another aspect of the disclosure here involves a method of treating a vein, the method including: inserting a medical device into the vein in a living body, the medical device including an elongated outer sheath, an inner member inside the outer sheath, possessing a distal end located more distally than the distal end of the outer sheath, and axially movable relative to the outer sheath, and an expansion portion between the distal end of the outer sheath and the distal end of the inner member. The expansion portion is expandable from a non-expanded position to an expanded position, and the inner member is prevented from proximal movement relative to the outer sheath when the medical device is inserted into the body with the expansion portion in the non-expanded position. The method further includes moving the medical device to position the medical device at a desired location in the vein while maintaining the expansion portion in the non-expanded position, applying a force on the inner member to move the inner member distally in an axial direction relative to the outer sheath, removing the force on the inner member to automatically axially move the inner member in a proximal direction relative to the outer sheath, and outwardly expanding the expansion portion as a result of the inner member moving in the proximal direction relative to the outer sheath.

BRIEF DESCRIPTION OF THE DRAWINGS

FIGS. 1A and 1B are plan views of a medical device according to a first embodiment disclosed here, wherein FIG. 1A depicts an initial state before expansion of an expansion portion, and FIG. 1B depicts an expanded state in which the expansion portion is expanded;

FIGS. 2A and 2B are sectional views of the medical device according to the first embodiment, wherein FIG. 2A depicts the initial state before expansion of the expansion portion, and FIG. 2B depicts the expanded state in which the expansion portion is expanded;

FIGS. 3A and 3B illustrate the medical device according to the first embodiment, wherein FIG. 3A is a partial perspective view, and FIG. 3B is a partial perspective sectional view;

FIGS. 4A and 4B are sectional views orthogonal to an axial direction of the medical device according to the first embodiment, wherein FIG. 4A is a sectional view taken along line B-B of FIG. 2A in the initial state, and FIG. 4B is a sectional view taken along line C-C of FIG. 2B in the expanded state;

FIGS. 5A and 5B are schematic views showing a knocking mechanism of the medical device according to the first embodiment, wherein FIG. 5A depicts the initial state, and FIG. 5B depicts a state in which a pushing portion has been pushed from the initial state;

FIGS. 6A and 6B are schematic views showing the knocking mechanism of the medical device according to the first embodiment, wherein FIG. 6A depicts a state in which the pushing portion has been pushed from the initial state, and FIG. 6B depicts the expanded state;

FIGS. 7A and 7B are schematic views showing the knocking mechanism of the medical device according to the first embodiment, wherein FIG. 7A depicts a state in which the pushing portion has been pushed from the expanded state, and FIG. 7B depicts the pushing portion returned to the initial state;

FIGS. 8A and 8B are schematic sectional views showing a state in which the medical device according to the first embodiment is inserted in a vein, wherein FIG. 8A depicts an initial state before expansion of the expansion portion, and FIG. 8B depicts an expanded state in which the expansion portion is expanded;

FIGS. 9A and 9B are schematic sectional views showing the state in which the medical device according to the first embodiment is inserted in the vein, wherein FIG. 9A depicts a state in which fluid has been released, and FIG. 9B depicts a state when a blood vessel wall is damaged by the expansion portion;

FIG. 10 is a schematic sectional view showing a modification of the medical device according to the first embodiment;

FIGS. 12A and 12B are plan views showing a further modification of the medical device according to the first embodiment, wherein FIG. 12A depicts the initial state before expansion of the expansion portion, and FIG. 12B depicts the expanded state in which the expansion portion is expanded;

FIGS. 14A and 14B are plan views of a medical device according to a second embodiment disclosed here, wherein FIG. 14A depicts an initial state before expansion of an expansion portion, and FIG. 14B depicts an expanded state in which the expansion portion is expanded;

FIGS. 15A and 15B are schematic sectional views showing a state in which the medical device according to the second embodiment is inserted in a vein, wherein FIG. 15A depicts an initial state before expansion of an expansion portion, and FIG. 15B depicts an expanded state in which the expansion portion is expanded;

FIGS. 16A and 16B are schematic sectional views showing a state in which the medical device according to the second embodiment is inserted in the vein, wherein FIG. 16A depicts a state in which fluid has been released, and FIG. 16B depicts a state in which a blood vessel wall is damaged by the expansion portion;

FIG. 17 is a schematic sectional view showing a modification of the medical device according to the second embodiment;

FIGS. 18A and 18B are plan views of a medical device according to a third embodiment disclosed here, wherein FIG. 18A depicts an initial state before expansion of an expansion portion, and FIG. 18B depicts an expanded state in which the expansion portion is expanded;

FIGS. 20A and 20B are plan views of a medical device according to a fourth embodiment disclosed here, wherein FIG. 20A depicts an initial state before expansion of an expansion portion, and FIG. 20B depicts an expanded state in which the expansion portion is expanded.

DETAILED DESCRIPTION

Figure 3A:
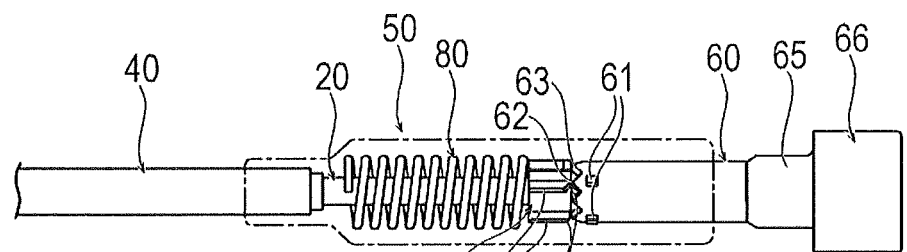

Non-limitative embodiments of the medical device disclosed here are described below, with references to the accompanying drawings. Note that dimensional ratios in the drawings may be exaggerated for convenience of explanation and may therefore be different from the actual ratios.

A medical device 10 according to a first embodiment is used for therapeutically treating (treatment) veins, particularly for occluding or reducing a varicose vein. Varicose veins occur mainly in lower limb veins, particularly in great saphenous veins and small saphenous veins, which are superficial veins. The varicose veins can also occur in pelvic, ovarian and spermatic cord veins. The medical device 10 is used to stimulate the inner wall of a vein by damaging the vein inner wall. The medical device may further treat the vein by injecting fluid such as a sclerosant or an adhesive into the vein to occlude the vein, thereby inhibiting backflow of blood. Note that herein the side toward which the device is inserted into a vein is referred to as the "distal side" (distal end) and the side of an operator's proximal operation is referred to as the "proximal side" (proximal end). An "initial state" is the state before expansion of an expansion portion.

The medical device 10, as shown in FIGS. 1A to 3B, includes a tubular inner tube 20 (inner member), a pipe shaped outer sheath 40 covering the inner tube 20, an expansion portion 30 capable of expansion and contraction (i.e., the expansion portion 30 is configured to expand and contract) at a distal portion of the medical device 10, and an operating portion 50 for operating the expansion portion 30.

The inner tube 20 includes a first lumen 21 for injection of fluid such as a sclerosant or an adhesive through the first lumen 21. Examples of the sclerosant or adhesive include polidocanol, sodium tetradecyl sulfate (STS), and cyanoacrylate. On the distal side in the inside of the inner tube 20, a core member 23 is embedded for imparting desirable rigidity to the inner tube 20. The core member 23 is gradually reduced in diameter from its proximal end to its distal end to be less rigid on the distal end to reduce the impact imposed on a living body that the medical device 10 contacts when inserted into a vein. The inner tube 20 has inner tube side holes 22 on the proximal side of the expansion portion 30, the inner tube side holes 22 piercing from the inner surface to the outer surface of the inner tube 20 (i.e., completely through the inner tube 20).

The outer sheath 40 is a tube shaped body covering the inner tube 20, and is axially movable relative to the inner tube 20. A distal end portion 41 of the outer sheath 40 is slidable in close contact with the outer peripheral surface of the inner tube 20, and a proximal end portion 42 of the outer sheath 40 is slidable in close contact with the outer peripheral surface of the inner tube 20. The outer sheath 40 possesses an outer sheath central portion between the distal end portion 41 and the proximal end portion 42 of the outer sheath. The outer sheath central portion 43 possesses a larger inside diameter than the inside diameter of the distal end portion 41 and the inside diameter of the proximal end portion 42 so that a predetermined gap is formed between the outer sheath central portion 43 and the outer peripheral surface of the inner tube 20 (i.e., a gap in the radial direction). The outer sheath central portion 43 is formed with a plurality of outer sheath side holes 44 piercing from the inner surface to the outer surface of the outer sheath central portion 43 (i.e., completely through the outer sheath), the outer sheath side holes 44 being aligned in the axial direction. A second lumen 45 is formed by the predetermined gap between the outer sheath central portion 43 and the outer peripheral surface of the inner tube 20. Fluid such as a sclerosant can flow from the first lumen 21 inside the inner tube 20 into the second lumen 45 via the inner tube side holes 22. Fluid in the second lumen 45 can then flow out to the exterior of the medical device 10 via the outer sheath side holes 44.

The expansion portion 30 has its distal end portion secured to a distal portion of the inner tube 20, and has its proximal end portion secured to the distal end portion 41 of the outer sheath 40. The expansion portion 30 possesses a plurality of spirally shaped linear material portions 31 (i.e., linear members that extend in the axial direction with a spiral curvature), which are aligned in the circumferential direction of the expansion portion 30. Each of the linear material portions 31 can be expanded while bending outward so as to come away from the outer peripheral surface of the inner tube 20 by proximal movement of the inner tube 20 relative to the outer sheath 40 (i.e., the linear material portions 31 can be compressed in the axial direction causing the linear material portion 31 to bend outwards in the radial direction). Each of the linear material portions 31 can also be contracted so as to come closer to the outer peripheral surface of the inner tube 20 by distal movement of the inner tube 20 relative to the outer sheath 40 starting from the expanded state (i.e., the linear material portions 31 can be elongated again in the axial direction to remove the outward bend in the radial direction). The linear material portions 31 may be formed by creating a plurality of spiral slits 32 in a tube shaped body. Note that the linear material portions 31 of the expansion portion 30 may also be formed by arranging discrete wires.

Figure 4A:
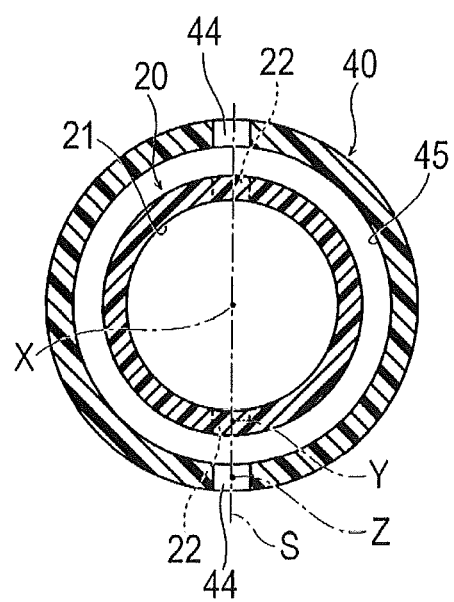
Figure 4B:
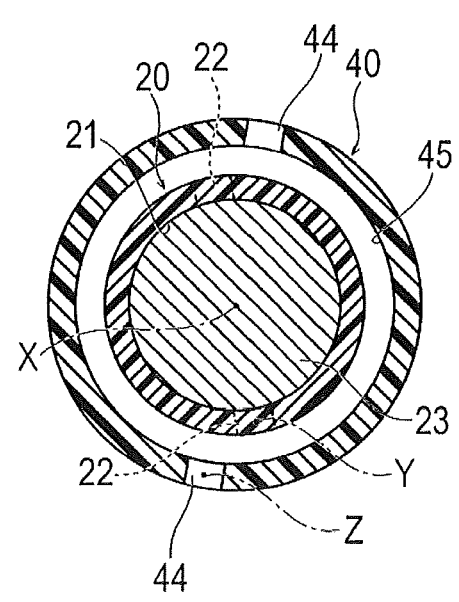

In this embodiment, the inner tube side holes 22 are located in the same axial location, but 180° apart in the circumferential direction. In a state in which the expansion portion 30 is expanded (i.e., the expanded state), the inner tube side holes 22 are located proximally of a distal-side boundary A1 of an axial range of formation of the outer sheath side holes 44 of the outer sheath 40 (i.e., the inner tube side holes 22 are proximal of the distal-most outer sheath side hole 44) and distally of a proximal-side boundary A2 of the axial range (i.e., the inner tube side holes 22 are distal of the proximal-most outer sheath side hole 44), and do not overlap with any of the outer sheath side holes 44 (i.e., the inner tube side holes 22 are misaligned from the outer sheath side holes 44 in both the axial and circumferential direction). In the expanded state of this embodiment, the inner tube side holes 22 are located in a substantially central portion of the axial range L over which the outer sheath side holes 44 are provided. Further, in the expanded state, the inner tube side holes 22 are not disposed on a line on which the outer sheath side holes 44 are aligned along the center axis X of the medical device 10 (i.e., the inner tube side holes 22 are not aligned with the outer sheath side holes 44 in the circumferential direction). As shown in the initial state depicted in FIG. 4A, in a section orthogonal to the direction of the center axis X of the medical device 10, a direction from the center axis X of the medical device 10 toward the outer sheath side holes 44 and a direction from the center axis X of the medical device 10 toward the inner tube side holes 22 coincide with each other (i.e., the outer sheath side holes 44 and the inner sheath side holes 22 are aligned in the circumferential direction as shown by the common axis S in FIG. 4A, which is orthogonal to the center axis X). In the expanded state shown in FIG. 4B, however, the outer sheath 40 has twisted, moving the positions of the outer sheath side holes 44 from their positions in the initial state, so that the direction from the center axis X of the medical device 10 toward the outer sheath side holes 44 and the direction from the center axis X of the medical device 10 toward the inner tube side holes 22 do not coincide with each other (i.e. the outer sheath side holes 44 and the inner sheath side holes 22 are misaligned in the circumferential direction).

In the medical device 10 configured as above, in the expanded state in which the expansion portion 30 is expanded, the inner tube side holes 22 are located proximally of the distal-side boundary A1 of the axial range L of formation of the outer sheath side holes 44 of the outer sheath 40 and distally of the proximal-side boundary A2 of the axial range L (i.e., axially towards the middle of the axial range L), so that fluid flowing through the inner tube side holes 22 moves in the manner of spreading to both sides in the axial direction, in reaching the outer tube side holes 44 (i.e., the fluid moves axially in both the proximal direction and distal direction after exiting the inner tube side holes 22). Therefore, the fluid can be released while minimizing the dispersion of the quantities of the fluid released out of the outer sheath side holes 44 (i.e., the fluid may be more evenly released from the outer sheath side holes 44). Accordingly, the inner wall surface of a vein can be damaged over a wide range and with minimized unevenness (i.e., the released fluid can more uniformly contact the inner wall surface of the vein in the axially direction). Consequently, the vein can be properly occluded or contracted.

The materials constituting the inner tube 20 and the outer sheath 40 are preferably materials which have hardness and flexibility. Examples of applicable materials include polyolefins such as polyethylene, polypropylene, etc., polyamides, polyesters such as polyethylene terephthalate, etc., fluoro-polymers such as ethylene tetrafluoroethylene (ETFE), etc., polyether-ether ketone (PEEK), polyimides, shape memory alloys provided with a shape memory effect or superelasticity by heat treatment, stainless steel, tantalum (Ta), titanium (Ti), platinum (Pt), gold (Au), tungsten (W), and so on. Preferable examples of the shape memory alloys include Ni—Ti alloys, Cu—Al—Ni alloys, and Cu—Zn—Al alloys. Metallic braids or coils may be added to the above-mentioned materials for the purpose of enhancing rigidity.

The material constituting the expansion portion 30 is preferably a material which has rigidity (hardness) and flexibility. Examples of a preferably usable material include polyolefins such as polyethylene, polypropylene, etc., polyamides, polyesters such as polyethylene terephthalate, etc., fluoro-polymers such as ETFE, etc., PEEK, polyimides, shape memory alloys provided with a shape memory effect or superelasticity by heat treatment, stainless steel, Ta, Ti, Pt, Au, W, and so on. Preferable examples of the shape memory alloys include Ni—Ti alloys, Cu—Al—Ni alloys, and Cu—Zn—Al alloys.

The length of the medical device 10 (the length from a distal-most portion of the inner tube 20 to the operating portion 50) is not particularly limited, but is preferably 100 mm to 1,000 mm, for example. The outside diameter of the outer sheath 40 is not specifically restricted, but is preferably 1.0 mm to 3.0 mm, for example. The inside diameter of the inner tube 20 is not particularly limited, but is preferably 0.3 mm to 1.0 mm, for example. The clearance (i.e., the predetermined gap) between the outer sheath 40 and the inner tube 20 where the second lumen 45 is formed is not specifically restricted, but is preferably 0.05 mm to 0.5 mm, for example. The maximum outside diameter of the expansion portion 30 in its expanded state is not particularly limited, but is preferably 3.0 mm to 20 mm, for example. The length of the range L over which the outer sheath side holes 44 of the outer sheath 40 are formed is not specifically restricted, but is preferably 50 mm to 200 mm, for example.

The expansion portion 30 and the core member 23 may be formed to contain a radiopaque material. This enables accurate grasping of positions, and hence an easier procedure, under radioscopy. Preferable examples of the radiopaque material include gold, platinum, platinum-indium alloy, silver, stainless steel, molybdenum, tungsten, tantalum, palladium, and alloys including these materials.

In addition, the expansion portion 30 and the core member 23 may be formed to include means for ultrasonic visual recognition. This enables accurate grasping of positions, and hence an easier procedure, during use of an ultrasonic diagnosis apparatus. Examples of the means for ultrasonic visual recognition include formation of ruggedness (i.e., a non-uniform surface) such as minute grooves or holes in the surface of the expansion portion 30 and the core member 23, and addition of porous material such as foam metal, cellular plastic, etc.

Besides, a marker composed of a radiopaque material may be disposed anywhere along either the inner tube 20 or the outer sheath 40, for example, at a portion of the inner tube 20 which is surrounded by the expansion portion 30. The marker may be provided at a desired position, for example, by winding a wire formed of a radiopaque material around the outer surface of the inner tube 20, or by attaching a pipe formed of a radiopaque material to the outer surface of the inner tube 20 by caulking or adhesion.

The operating portion 50 includes: an operating portion main body 51 to which a proximal end portion of the outer sheath 40 is connected; a pushing portion 60 axially movable relative to the operating portion main body 51; a rotatable body 70 capable of rotation (i.e., configured to rotate) inside the operating portion main body 51; and a coil spring 80 (biasing member) disposed inside the operating portion main body 51.

The pushing portion 60 is a portion for an operator to perform a pushing operation. The pushing portion 60 is biased proximally by the coil spring 80 (i.e., the coil spring 80 applies a proximal biasing force to the pushing portion 60) disposed inside the operating portion main body 51, and protrudes proximally out of the operating portion main body 51. An outer peripheral surface of the pushing portion 60 is formed with a plurality (in this embodiment, four) of rotation-restricting projections 61 (see FIG. 3A) at regular intervals (i.e., equally spaced in the circumferential direction). In addition, a distal end surface of the pushing portion 60 is formed with pluralities (in this embodiment, eight each) of triangular-shaped projections 62 and recesses 63 aligned at regular intervals, and in a zigzag pattern, along the circumferential direction. A tubular connection tube 64 is connected to a distal portion of the pushing portion 60, and a distal portion of the connection tube 64 is connected to a proximal portion of the inner tube 20. The pushing portion 60 is formed, at a proximal end portion, with an injection port 65 communicating with the first lumen 21 (i.e., fluid introduced into the injection port 65 may flow through the tubular connection tube 64 and into the first lumen 21). A cap 66 can be connected to the injection port 65 in a covering manner.

The rotatable body 70 has a plurality (in this embodiment, four) of engaging projections 71 on its outer peripheral surface (see FIG. 3A) at regular intervals (i.e., equally spaced in the circumferential direction). The engaging projection 71 is formed at a proximal end surface of the rotatable body 70 with an inclined surface 72, which is inclined against a plane orthogonal to the axial direction. The inclined surface 72 can make contact with the projection 62 and the recess 63.

Figure 3B:
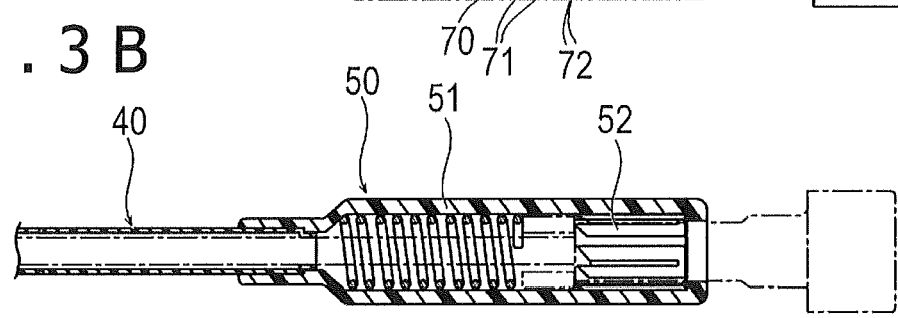

The operating portion main body 51 (body) is a tube shaped member, is connected on the distal side to a proximal end portion of the outer sheath 40, and is formed with a cam main body 52 at its inner peripheral surface (see FIG. 3B). The cam main body 52 is provided with a plurality (in this embodiment, four) of cam grooves 53 aligned at regular intervals in the circumferential direction (i.e., equally spaced in the circumferential direction). The cam groove 53 can accept the engaging projection 71 of the rotatable body 70 from the distal side, and is formed to extend in the axial direction.

Figure 5A:
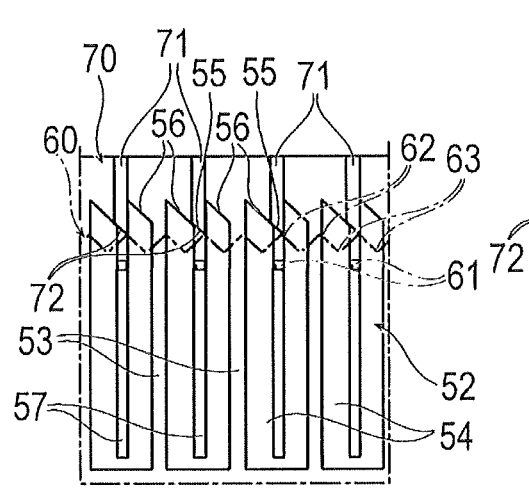

The schematic view (with respect to the circumferential direction) shown in FIG. 5A illustrates that between the adjacent cam grooves 53 of the cam main body 52, there is a wall portion 54 which projects from the inner peripheral surface. The wall portion 54 is formed with a fitting recess 55 at its distal end portion into which the engaging projection 71 can fit. On both sides of the fitting recess 55, there are inclined receiving surfaces 56 which are inclined in the same manner as the inclined surface 72 of the engaging projection 71. In addition, the operating portion main body 51 is formed with a plurality (in this embodiment, four) of rotation-restricting grooves 57 in which the rotation-restricting projections 61 of the pushing portion 60 are to be fitted in an axially movable manner (i.e., the rotation-restricting projections 61 are configured to axially move into the rotation-restricting grooves 57). The rotation-restricting projections 61 are moved only in the rotation-restricting grooves 57, so that the pushing portion 60 is not rotated relative to the operating portion main body 51.

Note that the cam grooves 53, the wall portions 54, the fitting recesses 55, the rotation-restricting grooves 57, the rotation-restricting projections 61, the engaging projections 71 and the like are provided in the numbers of four each, but the number of these components is not limited to four.

Now, a method of using the medical device 10 according to the first embodiment will be described, with the example case of occluding a vein V in the state of varicose vein occurring in a great saphenous vein or a small saphenous vein of the lower limb.

First, the medical device 10 is primed, flushing the inside of the first lumen 21 and the second lumen 45 with physiological salt solution. In this initial state, the expansion portion 30 is in a contracted state, and the cap 66 is put on the injection port 65.

In the case of occluding a great saphenous vein or a small saphenous vein, normally, an introducer sheath is inserted into the great saphenous vein or small saphenous vein by way of the knee which ensures easy access to the inside of the vein V. Thereafter, the medical device 10 prepared in the initial state is inserted through the introducer sheath into the vein V, starting from the distal end portion of the medical device 10. Note that the position at which to dispose the introducer sheath is not limited to the knee, and the insertion direction may be either an upstream direction or a downstream direction.

In the initial state, the engaging projections 71 of the rotatable body 70, being biased by the coil spring 80, are fitted in the distal-side fitting recesses 55 of the wall portions 54, as shown in FIG. 5A, and the expansion portion 30 is maintained in a contracted state (i.e., the non-expanded position). In other words, in the initial state, the knocking mechanism including the cam main body 52, the pushing portion 60 and the rotatable body 70 functions as a fixing portion which can fix the positions of the inner tube 20 and the outer sheath 40 (i.e., the fixing portion is configured to fix the inner tube 20 and the outer sheath 40 preventing either the inner tube 20 or outer sheath 40 to move relative to the other).

Next, the medical device 10 is pushed forward (i.e., moved distally) so that the expansion portion 30 is pushed in to the distal end of a treatment range for the vein V. The distal end of the treatment range may be, for example, the vicinity of a joining portion of the superficial vein side (the great saphenous vein or small saphenous vein) and a deep vein (e.g., a position deviated by 10 mm to 30 mm from the joint portion toward the superficial vein side). The medical device 10 is configured as shown in FIG. 8A such that the inner tube side holes 22 are not overlapping with the outer sheath side holes 44 in the initial state before expansion of the expansion portion 30. Therefore, excessive lowering in rigidity of the medical device 10 is obviated, and bending of the medical device 10 can be inhibited (i.e., the medical device 10 remains relatively rigid).

Figure 5B:
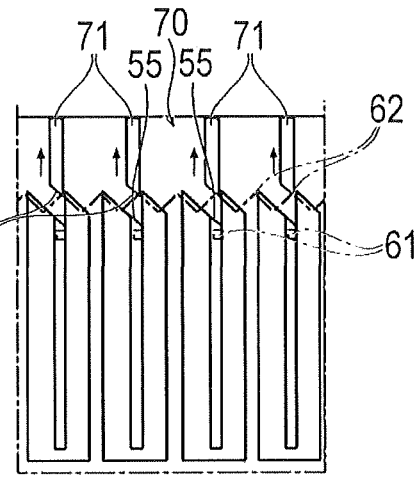

Subsequently, the pushing portion 60 is pushed distally relative to the operating portion main body 51 so that the projections 62 contact and push the inclined surfaces 72 of the engaging projections 71, as shown in FIG. 5B, so that the rotatable body 70 is moved distally while compressing the coil spring 80. In this instance, since the engaging projections 71 are fitted in the fitting recesses 55, the rotatable body 70 does not rotate inside the operating portion main body 51.

Figure 6A:
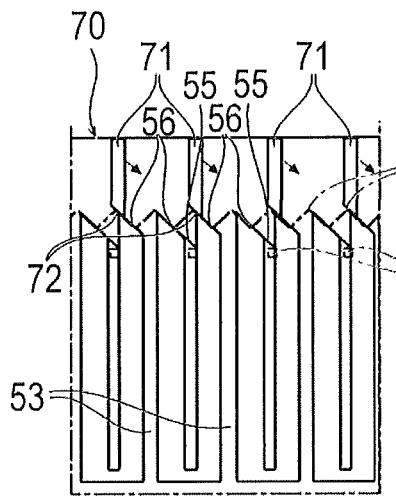
Figure 6B:
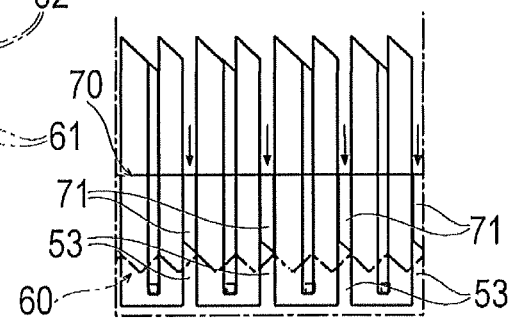

When the rotatable body 70 is moved distally and the engaging projections 71 reach positions distally of the fitting recesses 55, as shown in FIG. 6A, the engaging projections 71 under the biasing force of the coil spring 80 slide along the inclination of the projections 62 and the inclination of the inclined receiving surfaces 56. As a result, the rotatable body 70 rotates within the operating portion main body 51, and the engaging projections 71 arrive in the cam grooves 53. Thereafter, when the pushing of the pushing portion 60 is stopped and the pushing portion 60 is released by the user, the rotatable body 70 and the pushing portion 60 are pushed back proximally by the biasing force of the coil spring 80 (i.e., automatically without an external force being applied), so that the engaging projections 71 of the rotatable body 70 are moved proximally within the cam grooves 53, as shown in FIG. 6B. This movement is stopped when the rotatable body 70 is moved to a fixed position at which it becomes impossible for the rotatable body 70 to move proximally relative to the cam main body 52 (e.g., a position at which the engaging projections 71 arrive at the proximal ends of the cam grooves 53). The inner tube 20 is connected to the pushing portion 60 and thus moves proximally relative to the outer sheath 40 as the pushing portion 60 moves proximally. When the inner tube 20 moves proximally relative to the outer sheath, the expansion portion 30 expands to contact the inner wall surface of the vein V, as shown in FIG. 8B. The inner tube 20 stops moving proximally, and the expansion portion 30 stops expanding, once the rotatable body 30 reaches the fixed position. In the state in which the expansion portion 30 is expanded (i.e. the expanded state), the knocking mechanism including the cam main body 52, the pushing portion 60 and the rotatable body 70 is functioning as a fixing portion which is capable of fixing (i.e., configured to fix) the positions of the inner tube 20 and the outer sheath 40 relative to one another in the fixed position.

Next, as shown in FIG. 9A, the cap 66 is detached from the injection port 65. A syringe or the like in which fluid such as a sclerosant or adhesive is sealed (i.e., the syringe contains fluid) is connected to the injection port 65, and a predetermined amount of the fluid is injected. As a result, the fluid flows into the first lumen 21, then flows via the inner tube side holes 22 into the second lumen 45 of the outer sheath 40, and is released via the outer sheath side holes 44 to the exterior. In the expanded state in which the expansion portion 30 is expanded, the inner tube side holes 22 are located in a substantially central area within the range L over which the outer sheath side holes 44 are formed, and are located proximally of the distal-side boundary A1 of the range L and distally of the proximal-side boundary A2 of the range L (i.e., the inner tube side holes are distal of the proximal-most outer sheath side hole 44 and proximal of the distal-most outer sheath side hole 44). Therefore, unlike in the case where the fluid flows into the second lumen 45 via the proximal side or the distal side of the range over which the outer sheath side holes 44 are formed, the fluid moves through the inner tube side holes 22 and spreads (i.e., disperses) to both sides in the axial direction to reach the outer sheath side holes 44. For this reason, the fluid can be released while minimizing the dispersion of the quantities of the fluid released through the respective outer sheath side holes 44 (i.e., the fluid is released approximately evenly from each of the outer sheath side holes 44), and the inner wall surface of the vein V can be damaged over a wide range and with minimized unevenness. Consequently, the vein V can be properly occluded or contracted. In the expanded state, in a section parallel to the center axis X of the medical device 10, the position at which the inner tube side holes 22 are aligned along the center axis X and the position at which the outer sheath side holes 44 are aligned along the center axis X do not coincide with each other, and the inner tube side holes 22 and the outer sheath side holes 44 are disposed at such positions as not to overlap with each other in the direction of the center axis X (i.e., the inner tube side holes 22 do not axially or circumferentially align with the outer sheath side holes 44). Therefore, it takes some time for the fluid having passed through the inner tube side holes 22 to reach the outer sheath side holes 44, so that dispersion of the quantities of the fluid released through the respective outer sheath side holes 44 can be minimized.

In addition, even if the inner tube side holes 22 are positioned on a straight line on which the outer sheath side holes 44 are aligned in the initial state (i.e., the inner tube side holes 22 are circumferentially aligned with the outer sheath side holes 44), a twisting force is generated between the inner tube 20 and the outer sheath 40 by elastic forces of the linear material portions 31 at the time of expansion of the linear material portions 31 which are spirally shaped. Therefore, it can be ensured that in the initial state, in a section orthogonal to the center axis X of the medical device 10, the center axis X of the medical device 10, an inner tube side hole axis Y configured by alignment of the inner tube side holes 22 in the direction of the center axis X, and an outer sheath side hole axis Z configured by alignment of the outer sheath side holes 44 in the direction of the center axis X are positioned on the same line S (see FIG. 4A), whereas in the state in which the expansion portion 30 is expanded, the outer sheath 40 has been twisted and the positions of the outer sheath side holes 44 have been moved from those in the initial state (see FIG. 4B) so that the center axis X, the inner tube side hole axis Y and the outer sheath side hole axis Z are not positioned on the same line (i.e., the outer sheath side holes 44 no longer circumferentially align with the inner tube side holes 22). In addition, when the inner tube 20 of the medical device 10 in the initial state is moved proximally relative to the outer sheath 40, the outer sheath 40 is twisted due to the contact between the blood vessel inner wall and the spirally shaped linear material portions 31 of the expansion portion 30. For these reasons, it takes some time for the fluid having passed through the inner tube side holes 22 to reach the outer sheath side holes 44, so that dispersion of the quantities of the fluid released through the respective outer sheath side holes 44 can be minimized. Note that the center axis X, the inner tube side hole axis Y and the outer sheath side hole axis Z may not be positioned on the same line S in the initial state.

Subsequently, when the operating portion 50 is pulled (i.e., moved proximally) by the user, the expansion portion 30 is moved inside the vein V while damaging the inner wall surface of the vein V, as shown in FIG. 9B. In this instance, since the expansion portion 30 is provided with the spirally shaped linear material portions 31, the inner wall surface of the vein V can be damaged over the wide range L and evenly. The traveling distance of the expansion portion 30 is preferably not greater than the length of the range L over which the outer sheath side holes 44 are formed (for example, 100 mm), or within the range over which the sclerosant or adhesive is released. As a result, the sclerosant or adhesive comes into contact with the damaged blood vessel wall, to cause inflammation, thrombus formation, or growth of smooth muscle cells in the blood vessel wall, whereby the vein V can be occluded effectively.

Thereafter, a predetermined amount of the fluid (sclerosant or adhesive) is again injected via the injection port 65, and the expansion portion 30 is moved within the range of release of the fluid to damage the blood vessel, to occlude the vein V. This operation is repeated, whereby the vein V over a desired range can be entirely occluded.

Since the expansion portion 30 is elastically deformable (i.e., compressible), the size of the expansion portion 30 is appropriately varied (i.e., the size of the outside diameter of the expansion portion may compress or expand) according to variations in the inside diameter of the vein V, whereby an appropriate damage can always be given to the vein V. Alternatively, the rigidity of the coil spring 80 may be controlled (i.e., preset) so that the expansion portion 30 can always maintain a suitable size, whereby it is ensued that the inner tube 20 receiving a force from the expansion portion 30 deformed according to a variation in the inside diameter of the vein V can be moved relative to the outer sheath 40, as shown in FIG. 10 (i.e., the coil spring 80 expands and compresses along the center axis of the catheter as the outside diameter of the expansion portion 30 expands and compresses to the necessary size to contact the inner surface wall of the vein V). In this case, the coil spring 80 is automatically expanded and contracted by the force received from the inner tube 20. For example, when the medical device 10 is moved proximally in the condition where the elastic force of the coil spring 80 is weaker than the elastic force of the expansion portion 30, the expansion portion 30 is radially contracted according to the diameter of the blood vessel inner wall, and the inner tube 20 is moved distally by a distance corresponding to the contraction of the expansion portion 30, so that the pushing portion 60 is also moved simultaneously, and the coil spring 80 is automatically contracted distally.

Figure 7A:
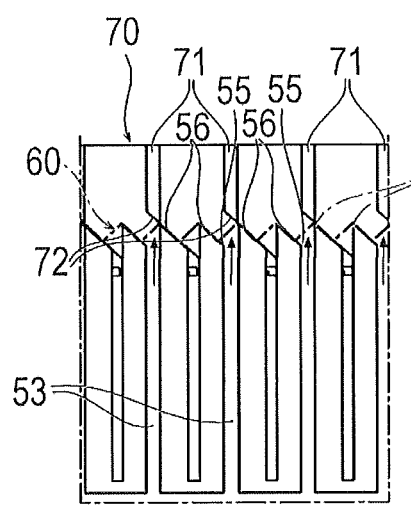

After the treatment of the vein V over the desired range is completed, the syringe or the like is detached from the injection port 65, the cap 66 is put on the injection port 65, and the pushing portion 60 is pushed in (i.e., moved distally) relative to the operating portion main body 51 causing the projections 62 of the pushing portion 60 to contact and push the inclined surfaces 72 of the engaging projections 71, as shown in FIG. 7A. This pushing force moves the rotatable body 70 distally while compressing the coil spring 80. In this instance, since the engaging projections 71 are fitted in the cam grooves 53, the rotatable body 70 does not rotate inside the operating portion main body 51.

Figure 7B:
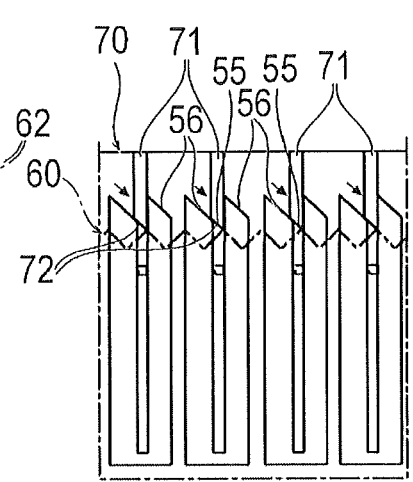

When the rotatable body 70 is moved distally and the engaging projections 71 reach positions distally of the cam grooves 53, the engaging projections 71 under a reaction force of the coil spring 80 slide along the inclination of the projections 62 and the inclination of the inclined receiving surfaces 56, whereby the rotatable body 70 is rotated. Thereafter, when the pushing of the pushing portion 60 is stopped and the pushing portion 60 is released by the user, the rotatable body 70 and the pushing portion 60 are pushed back proximally by the reaction force of the coil spring 80, and the engaging projections 71 are fitted into the fitting recesses 55, as shown in FIG. 7B, whereby a state in which the expansion portion 30 is contracted is maintained. Thus, the pushing portion 60 is functioning also as a releasing portion for releasing the state in which the positions of the inner tube 20 and the outer sheath 40 are fixedly maintained, through the fitting of the engaging projections 71 in the fitting recesses 55.

Thereafter, the medical device 10 is pulled out of the introducer sheath, and the introducer sheath is pulled out of the vein V, whereby the procedure is completed.

As has been described above, the medical device 10 according to the first embodiment includes: the elongated outer sheath 40 (the elongated outer sheath 40 can be the operating portion 51); the inner tube 20 (inner member) which extends through the inside of the outer sheath 40 and protrudes distally beyond the outer sheath 40; the expansion portion 30 which is positioned between a distal portion of the outer sheath 40 and a distal portion of the inner tube 20, is provided with the plurality of linear material portions 31 extending along the axial direction of the inner tube 20, and is expandable while bending in the radial direction of the inner tube 20 by moving the inner tube 20 proximally relative to the outer sheath 40; the coil spring 80 (biasing member) which is disposed inside the outer sheath 40 and which biases the inner tube 20 proximally relative to the outer sheath 40; the fixing portion (the cam main body 52, the pushing portion 60 and the rotatable body 70) which is capable of fixing the positions of the inner tube 20 and the outer sheath 40 in the state in which the expansion portion 30 has been expanded by moving the inner tube 20 proximally relative to the outer sheath 40 while deforming (i.e., compressing) the coil spring 80; and the pushing portion 60 (releasing portion) which enables the fixed state at the fixing portion to be released by distally pushing the pushing portion 60. Therefore, the medical device 10 according to the first embodiment makes it possible to easily maintain the expanded state of the expansion portion 30 by the fixing portion, and to release the fixed state by pushing (i.e., distally moving) only the pushing portion 60 (i.e., the outer sheath 40 could be moved distally relative to the inner tube 20 instead of moving the inner tube 20 proximally relative to the outer sheath). Thus, according to the medical device 10, the expansion portion 30 can be expanded into and contracted from a suitable state by easy operations.

In addition, in the state in which the expansion portion 30 is expanded (i.e., the expanded state), the fixing portion stops proximal movement of the inner tube 20 (inner member) relative to the outer sheath 40 in the fixed position and, at the same time, permits the inner tube 20 to be moved distally relative to the outer sheath 40 by contraction of the expansion portion 30 so as to deform (i.e., compress) the coil spring 80. Therefore, the expansion portion 30 can be deformed while permitting the coil spring 80 to be deformed according to variations in the inside diameter of the vein V.

The inner tube 20 (inner member) and the outer sheath 40 are formed with the first lumen 21 and the second lumen 45 through which fluid can flow, and the outer sheath 40 is formed with the outer sheath side holes 44 piercing the wall of the outer sheath 40 sideways (i.e., orthogonal to the axial direction) for releasing the fluid out of the second lumen 45. For this reason, the fluid can be released to appropriate positions of the vein V.

In addition, the fixing portion for fixing the positions of the inner tube 20 and the outer sheath 40 includes: the cam main body 52 connected to the outer sheath 40; the pushing portion 60 capable of pushing the inner tube 20 distally; and the rotatable body 70 capable of rotating (i.e., configured to rotate) inside the cam main body 52. The rotatable body 70 is formed with the engaging projections 71 projecting at the outer peripheral surface of the rotatable body 70. The cam main body 52 is a tubular member. The cam main body 52 possesses the cam grooves 53 at its inner wall surface, the cam grooves 53 extending in the axial direction. The cam main body also possesses the fitting recesses 55 in which the engaging projections 71 can be fitted. The cam main body 52 is formed, at its distal end surface, with the inclined surfaces 72 for guiding the engaging projections 71 in the circumferential direction. The pushing portion 60 possesses the pluralities of projections 62 and recesses 63 aligned in the circumferential direction at the distal end surface of the pushing portion. In the initial state in which the expansion portion 30 is contracted (i.e., in the non-expanded position or in the non-expanded state), the engaging projections 71 are fitted in the fitting recesses 55. When the pushing portion 60 is pushed distally starting from the initial state, the projections 62 move the engaging projections 71 distally to disengage the engaging projections 71 from the fitting recesses 55. The biasing force of the coil spring 80 then causes the engaging projections 71 to slide along the inclined surface 72 to be guided into the cam grooves 53 while the rotatable body 70 correspondingly rotates. When the pushing of the pushing portion 60 is stopped in the condition where the engaging projections 71 have been guided into the cam grooves 53 and the pushing portion 60 is released by the user, the engaging projections 71 automatically move proximally along the cam grooves 53. This proximal movement of the pushing portion 60 causes the inner tube 20 to move proximally relative to the outer sheath 40, and the expansion portion 30 to expand into the expanded state to contact the inner wall surface of the vein V. When the pushing portion 60 is pushed distally starting from the expanded state, the projections 62 move the engaging projections 71 distally to disengage the engaging projections 71 from the cam grooves 53. The biasing force of the coil spring 80 then causes the engaging projections 71 to slide along the inclined surfaces 72 to be guided into the fitting recesses 55 while the rotatable body 72 is rotated correspondingly. With such a configuration, it is possible to easily switch between the expanded state and the contracted state (i.e., between the expanded position and the non-expanded position) of the expansion portion 30, by only pushing the pushing portion 60 in a repeated manner (i.e., the outer sheath 40 could be moved distally relative to the inner tube 20 instead of moving the inner tube 20 proximally relative to the outer sheath). This configuration thus enhances operability of the medical device 10.

In the medical device 10 according to the first embodiment, in the expanded state in which the expansion portion 30 is expanded, the inner tube side holes 22 are positioned proximally of the distal-side boundary A1 of the axial range of formation of the outer sheath side holes 44 of the outer sheath 40 and distally of the proximal-side boundary A2 of the axial range. Therefore, the fluid can be released while minimizing the dispersion of the quantities of the fluid released through the respective outer sheath side holes 44. Accordingly, the inner wall surface of the vein V can be damaged over a wide range and with minimized unevenness (i.e., the fluid can be dispersed more evenly), and the vein V can be occluded properly.

In addition, in the expanded state in which the expansion portion 30 is expanded, the inner tube side holes 22 are so positioned as not to overlap with but to be staggered from the outer sheath side holes 44, so that dispersion of the quantities of the fluid released through the respective outer sheath side holes 44 can be reduced. Consequently, the fluid can be released over a maximized axial range and with minimized unevenness (i.e., the fluid can be dispersed more evenly).

Since all the inner tube side holes 22 are located proximally of the distal-most outer sheath side hole 44 and distally of the proximal-most outer sheath side hole 44, the fluid having passed through the inner tube side holes 22 moves in the manner of spreading to both distal and proximal sides in reaching the outer sheath side holes 44. Therefore, the fluid can be released while minimizing the dispersion of the quantities of the fluid released through the respective outer sheath side holes 44. Accordingly, the inner wall surface of the vein V can be damaged over a wide range and with minimal unevenness (i.e., the fluid can be dispersed more evenly), and the vein V can be properly occluded or contracted.

Forming the linear material portions 31 spirally causes the outer sheath 40 to be twisted relative to the inner tube 20 at the time of expansion of the linear material portions 31 due to the relative movement of the inner tube 20 and the outer sheath 40 or at the time of proximal movement of the medical device 10 with the linear material portions 31 in contact with an object of contact (e.g., the inner wall surface of the vein V). Therefore, the positions of the inner tube side holes 22 and the outer sheath side holes 44 can be staggered from each other so that they do not overlap. As a result, it takes some time for the fluid having passed through the inner tube side holes 22 to reach the outer sheath side holes 44. Accordingly, the dispersion of the quantities of the fluid released through the respective outer sheath side holes 44 can be minimized, and the inner wall surface of the vein V can be damaged over a wide range and with minimal unevenness (i.e., the fluid can be dispersed more evenly).

In the initial state before expansion of the expansion portion 30, the inner tube side holes 22 may be positioned to overlap with the outer sheath side holes 44 (i.e., align in the axial and circumferential directions). This ensures that in the priming before use of the medical device 10, physiological salt solution or the like is easily drained through the inner tube side holes 22 and the outer sheath side holes 44, the pressures inside the first lumen 21 and the second lumen 45 can be prevented from becoming excessively high, and the priming load can be alleviated. Due to the overlapping between the inner tube side holes 22 and the outer sheath side holes 44 in the initial state, the corresponding holes communicate with each other to provide a greater overall hole depth, whereby ultrasonic visual recognition properties are enhanced. Consequently, it becomes easier to confirm the positions of the inner tube side holes 22 and the outer sheath side holes 44 before injecting fluid into the first lumen 21.

Figure 11:
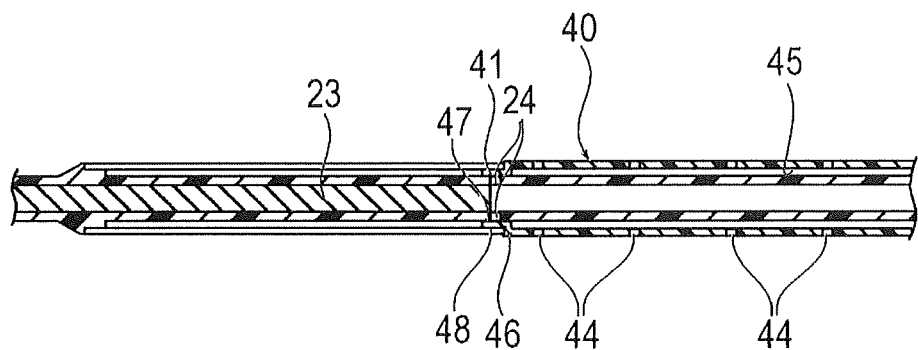
FIG. 11 is a schematic sectional view showing another modification of the medical device according to the first embodiment.

In a modification of the first embodiment, in the initial state before expansion of the expansion portion 30, the inner tube side holes 24 may be located distally of the outer sheath side holes 44 and be covered by the distal end portion 41 of the outer sheath 40, as shown in FIG. 11. With the inner tube side holes 24 thus sealed by the distal end portion 41 in the initial state, it becomes difficult for the fluid such as a sclerosant or adhesive to leak from the inner tube 20 before expansion of the expansion portion 30, so that the fluid can be effectively released after expansion of the expansion portion 30. In the initial state, a step 46 is formed at the distal end portion 41 of the outer sheath 40. An outer surface 48 of the step 46 is in contact with the expansion portion 30 (i.e., at the proximal end of the expansion portion 30), whereas an inner surface 47 of the step 46 is covering the inner tube side holes 22. In the expanded state, the inner tube side holes 22 are moved a distance equal to that of a relative movement of the inner tube 20 and the outer sheath 40. In this instance, the outer surface 48 of the step 46 at the distal end portion 41 is in contact with the expansion portion 30, whereas the inner surface 47 of the step 46 is in contact with the inner tube 20, so that the portion at which the step 46 is provided is strengthened in rigidity (i.e., the portion at which the step 46 is provided possesses higher rigidity than if the step 46 were not provided), and a large change in rigidity is present in the vicinity of the inner surface 47. However, since the core member 23 is moved proximally by a distance corresponding to the expansion of the expansion portion 30 from its position in the initial state, the core member 23 is positioned on the inside of the portion at which the rigidity changes, and bending at the rigidity changing portion can be inhibited. Furthermore, with the core member 23 disposed on the inside of the expansion portion 30 in the expanded state, the expansion portion 30 can be moved in a stable manner, so that the blood vessel wall surface (e.g., the inner wall surface of the vein V) can be properly damaged. Note that the inner tube side holes 24 may be covered not with the distal end portion 41 (sealing member) of the outer sheath 40 but with a sealing member attached as a separate member to the inner peripheral surface of the outer sheath 40. The sealing member may be ring shaped, or may be provided partly in the circumferential direction according to the portion at which the inner tube side holes 22 are formed. The number of the sealing members is not particularly limited. The material constituting the sealing member is not particularly limited, and examples of the material include synthetic resin elastomers such as olefin elastomers (e.g., polyethylene elastomer, polypropylene elastomer), polyamide elastomers, styrene elastomers (e.g., styrene-butadiene-styrene copolymer, styrene-isoprene-styrene copolymer, styrene-ethylenebutylene-styrene copolymer), polyurethane, urethane elastomers, fluoro-resin elastomers, etc., and rubbers such as synthetic rubbers such as urethane rubber, silicone rubbers, butadiene rubber, etc., and natural rubbers such as latex rubber, etc.

Figure 12A:
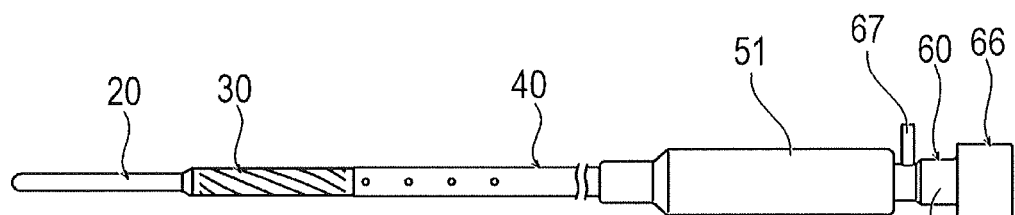
Figure 12B:
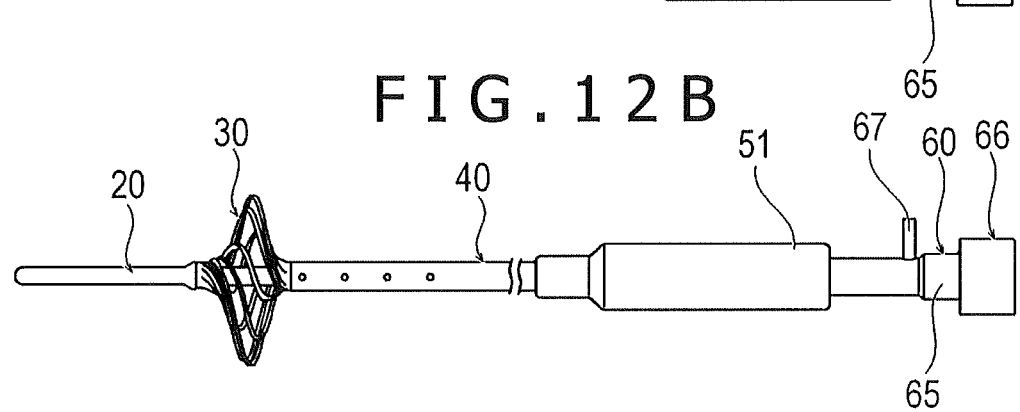

In another modification of the first embodiment, the pushing portion 60 may be provided with an operating projection 67 projecting sideways, as shown in FIGS. 12A and 12B. According to such a configuration, the operating projection 67 can be utilized at the time of pushing the pushing portion 60, which eliminates the need to connect a syringe or the like to the injection port 65. Consequently, operability and safety can be enhanced.

Figure 13:
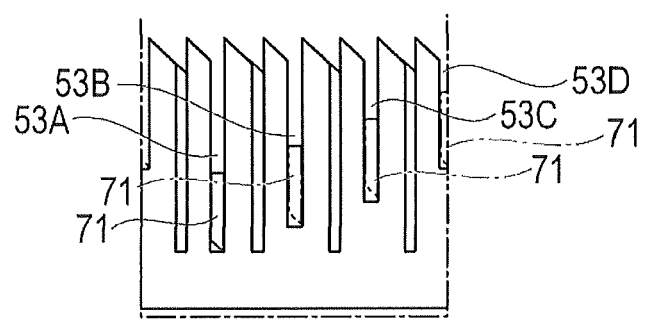
FIG. 13 is a schematic view of a knocking mechanism in another modification of the medical device according to the first embodiment.

In a further modification of the first embodiment, four cam grooves 53A, 53B, 53C, and 53D may be different in axial length, as shown in FIG. 13. In addition, the number of the engaging projections 71 capable of being fitted in the cam grooves 53A, 53B, 53C, and 53D (i.e., configured to fit within and engage with) is only one instead of four. According to such a configuration, the positional relation (i.e., relative position) between the inner tube 20 and the outer sheath 40 in the expanded state varies according to the length of that one of the cam grooves 53A, 53B, 53C, and 53D in which the engaging projection 71 is fitted. Therefore, by repeating knocking of the pushing portion 60, the engaging projection 71 can be selectively fitted into the cam grooves 53A, 53B, 53C, and 53D different in length, thereby changing the size of the expansion portion 30. Thus, the fixing portion capable of fixing (i.e., configured to fix) the positions of the inner tube 20 and the outer sheath 40 is capable of fixing the expansion portion 30 in a plurality of different sizes. As a result, it is possible to appropriately select a desirable size for the expansion portion 30, according to the conditions of a vein V to be treated.

In another aspect, there is also disclosed a method of treating (therapeutically treating) a vein. The treating method is performed by a medical device, the medical device including: an elongated outer sheath; an inner member extending through the inside of the outer sheath, the inner member protruding distally beyond the outer sheath; an expansion portion located between a distal portion of the outer sheath and a distal portion of the inner member, the expansion portion having a plurality of linear material portions extending in an axial direction of the inner member, the expansion portion being expandable while bending in a radial direction of the inner member by moving the inner member proximally relative to the outer sheath; a biasing member disposed inside the outer sheath, the biasing member biasing the inner member proximally relative to the outer sheath; a fixing portion capable of fixing positions of the inner member and the outer sheath in a condition where the expansion portion has been expanded by moving the inner member proximally relative to the outer sheath while deforming the biasing member; and a releasing portion capable of releasing the fixed state at the fixing portion by pushing thereof in a predetermined direction, wherein the inner member or the outer sheath is formed with a lumen through which fluid can flow, and is formed with a side hole piercing the inner member or outer sheath sideways for releasing the fluid from the lumen to the outside. In addition, this treating method includes: (i) a step of inserting into a vein the medical device with the expansion portion in a contracted state; (ii) a step of moving the inner member in an axial direction relative to the outer sheath to expand the expansion portion, to make the expansion portion contact an inner wall surface of the vein, and to fix the positions of the inner member and the outer sheath in the expanded state by the fixing portion; (iii) a step of releasing fluid through the side holes into the vein; (iv) a step of moving the expansion portion in the expanded state inside the vein to damage the inner wall surface of the vein; (v) a step of contracting the expansion portion; and (vi) a step of withdrawing the medical device out of the vein. The treating method makes it possible to make fluid such as a sclerosant or an adhesive act on the inner wall surface of the vein damaged by the expansion portion, thereby causing inflammation, thrombus formation, or growth of smooth muscle cells in the blood vessel wall, and achieving effective treatment of the vein. Note that the treatment of a vein includes therapy by occluding the vein. In the aforementioned treating method, the step of releasing the fluid via the side holes into the vein may be carried out before or after the step of damaging the inner wall surface of the vein.

In the aforementioned treating method, the step of releasing the fluid into the vein through outer sheath side holes (side holes) and the step of damaging the inner wall surface of the vein may be conducted alternately and repeatedly. Alternate repetition of these steps makes it possible to treat a vein over a wide range.

In addition, in the step of expanding the expansion portion in the aforementioned treating method, the expansion portion may be expanded to a size selected from a plurality of different sizes. Where the size of the expansion portion can be selected, a desirable size for the expansion portion can be appropriately selected according to the conditions of a vein to be treated.

Another method of treating a vein is conducted by a medical device, the medical device including: an elongated outer sheath possessing outer sheath side holes piercing from an inner surface to an outer surface of a distal portion of the elongated outer sheath; an inner tube extending through the inside of the outer sheath, the inner tube being formed in a distal portion thereof with inner tube side holes piercing from an inner surface to an outer surface of the distal portion, the inner tube protruding distally beyond the outer sheath; and an expansion portion located between a distal portion of the outer sheath and a distal portion of the inner tube, the expansion portion being provided with a plurality of linear material portions extending in the axial direction of the inner tube, the expansion portion being expandable while bending in the radial direction of the inner tube by moving the inner tube proximally relative to the outer sheath, wherein in an expanded state in which the expansion portion is expanded, the inner tube side holes are positioned proximally of a distal-side boundary of an axial range over which the outer sheath side holes of the outer sheath are formed and distally of a proximal-side boundary of the axial range. In addition, this treating method includes: (i) a step of inserting into a vein the medical device with the expansion portion in a contracted state; (ii) a step of moving the inner tube in the axial direction relative to the outer sheath to expand the expansion portion and make the expansion portion contact an inner wall surface of the vein; (iii) a step of causing fluid to flow into the outer sheath via the inner tube side holes positioned proximally of the distal-side boundary of the range over which the outer sheath side holes of the outer sheath are formed and distally of the proximal-side boundary of the range, and then releasing the fluid via the outer sheath side holes into the vein; (iv) a step of moving the expansion portion in the expanded state inside the vein to damage the inner wall surface of the vein; (v) a step of contracting the expansion portion; and (vi) a step of withdrawing the medical device out of the vein. It is possible by the treating method to release the fluid while minimizing the dispersion of the quantities of the fluid released through the respective outer sheath side holes. Consequently, the inner wall surface of a vein can be damaged over a wide range and with minimized unevenness, and the vein can be occluded properly.

The method of treating the vein disclosed here thus includes: inserting a medical device into the vein in a living body, the medical device including an elongated outer sheath, an inner member inside the outer sheath, possessing a distal end located more distally than the distal end of the outer sheath, and axially movable relative to the outer sheath, and an expansion portion between the distal end of the outer sheath and the distal end of the inner member. The expansion portion is expandable from a non-expanded position to an expanded position, and the inner member is prevented from proximal movement relative to the outer sheath when the medical device is inserted into the body with the expansion portion in the non-expanded position. The method further includes moving the medical device to position the medical device at a desired location in the vein while maintaining the expansion portion in the non-expanded position, applying a force on the inner member to move the inner member distally in an axial direction relative to the outer sheath, removing the force on the inner member to automatically axially move the inner member in a proximal direction relative to the outer sheath, and outwardly expanding the expansion portion as a result of the inner member moving in the proximal direction relative to the outer sheath.

A medical device 90 according to a second embodiment differs from the first embodiment in only the configuration of an operating portion 100. The portions having the same or equivalent functions to those of the portions in the first embodiment above will be denoted by the same reference symbols as used above, and descriptions of such portions will be omitted.

The operating portion 100 of the medical device 90 according to the second embodiment, as shown in FIGS. 14A to 15B, includes an operating portion main body 101 to which a proximal portion of an outer sheath 40 is connected, a pushing portion 110 axially movable relative to the operating portion main body 101, and a coil spring 80 (biasing member) disposed inside the operating portion main body 101.

The pushing portion 110 is a portion for an operator to perform a pushing operation. The pushing portion 110 is biased proximally by the coil spring 80 disposed inside the operating portion main body 101, and protrudes proximally from the operating portion main body 101. The pushing portion 110 includes a rotation-restricting projection (not shown) at an outer peripheral surface of the pushing portion 110. In addition, the pushing portion 110 includes an engaging portion 111 projecting radially outward of the outer peripheral surface at the distal end of the pushing portion. The engaging portion 111 is formed in a cantilever form, and can be moved so as to bend radially inward. The engaging portion 111 has a distal end surface formed to be inclined against a plane orthogonal to the center axis of the pushing portion 110, and has a proximal-side surface formed to be substantially parallel to the plane orthogonal to the center axis of the pushing portion 110. A pipe shaped connection tube 112 is connected to a distal portion of the pushing portion 110, and a distal portion of the connection tube 112 is connected to a proximal portion of an inner tube 20.

The operating portion main body 101 is a tubular member, which is connected on the distal side to a proximal portion of the outer sheath 40. The inner surface of the operating portion main body 101 has a rotation-restricting groove (not shown) in which the rotation-restricting projection of the pushing portion 110 is fitted in an axially movable manner. Since the rotation-restricting projection formed at the outer peripheral surface of the pushing portion 110 is moved only within the rotation-restricting groove, the pushing portion 110 is not rotated relative to the operating portion main body 101.

The operating portion main body 101 is formed with two through-holes, namely, a first through-hole 102 (fitting recess) and a second through-hole 103, which are aligned in the axial direction. The first through-hole 102 and the second through-hole 103 are formed to pierce from an inner surface to an outer surface of the operating portion main body 101, and the engaging portion 111 can engage through the first through-hole 102 and the second through-hole 103 from the inner surface side.

The operating portion main body 101 is formed with a cantilever-shaped pushing-out portion 104, which is formed to extend from the proximal side toward the distal side. The pushing-out portion 104 can come into the first through-hole 102 from the outer surface side, by bending.

An operation of the medical device 90 according to the second embodiment will be described below.

Figure 14A:
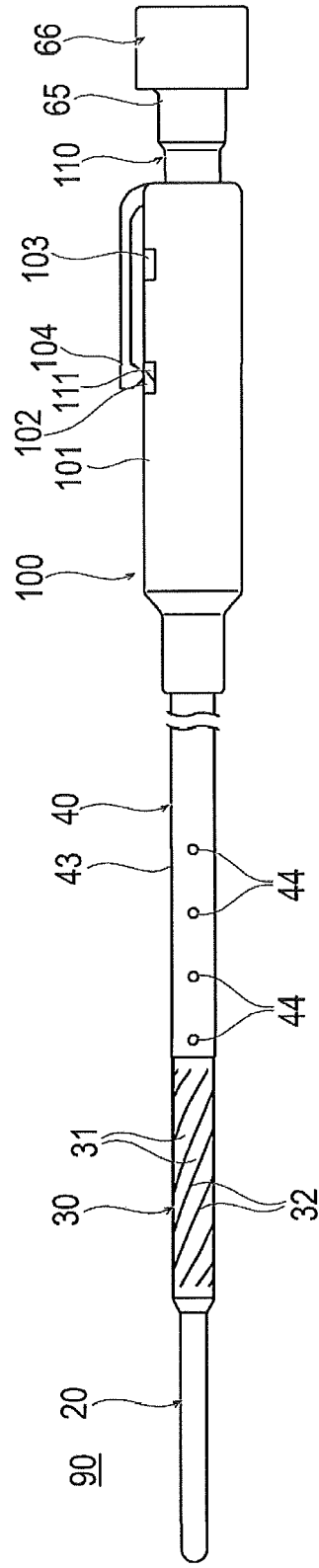

The medical device 90 is configured so that in an initial state in which an expansion portion 30 is contracted (i.e., a non-expanded position), the engaging portion 111 of the pushing portion 110 is fitted in the first through-hole 102, as shown in FIGS. 14A and 15A. In this instance, since the proximal-side surface of the engaging portion 111 is formed to be substantially parallel to the plane orthogonal to the center axis of the pushing portion 110, the engaging portion 111 (which is biased proximally by the coil spring 80) is caught on an edge of the first through-hole 102. This configuration prevents proximal movement of the engaging portion and thus maintains an initial state with the expansion portion 30 in the contracted state (i.e., the non-expanded position).

Figure 14B:
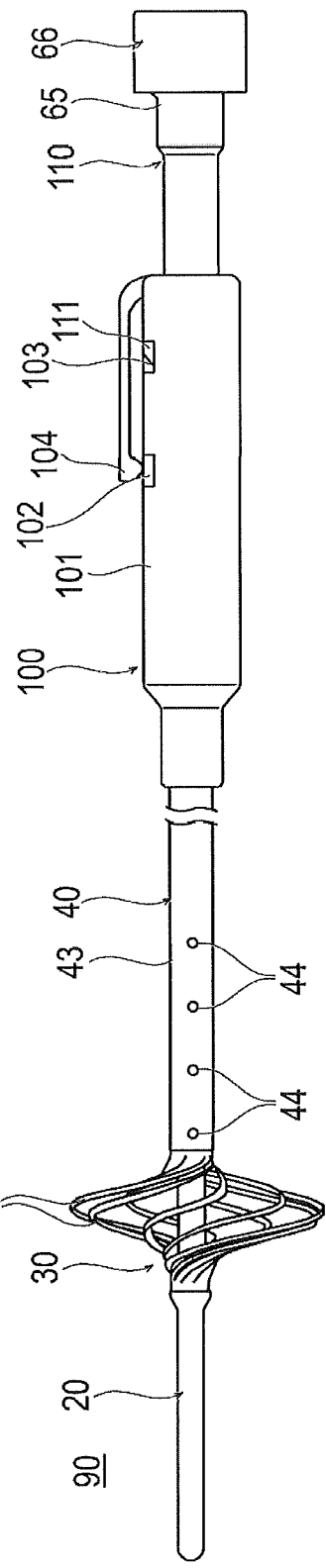

When the pushing-out portion 104 is pushed from the outer surface side in the initial state, the pushing-out portion 104 comes into the first through-hole 102, as shown in FIGS. 14B and 15B, to push the engaging portion 111 present in the first through-hole 102 to the inner side out of the first through-hole 102, so that the engaging portion 111 is disengaged from the first through-hole 102. When the engaging portion 111 is disengaged from the first through-hole 102, a biasing force of the coil spring 80 causes the pushing portion 110 to move proximally relative to the operating portion main body 101, and the expansion portion 30 is expanded (i.e., into the expanded position). The engaging portion 111 dislodged from the first through-hole 102 is fitted into the second through-hole 103 formed on the proximal side of the first through-hole 102. In this instance, since the proximal-side surface of the engaging portion 111 is formed to be substantially parallel to the plane orthogonal to the center axis of the pushing portion 110, the engaging portion 111 which is biased proximally by the coil spring 80 is caught on an edge of the second through-hole 103, whereby an expanded state in which the expansion portion 30 is expanded is maintained. Under this condition, as shown in FIG. 16A, a cap 66 is detached, fluid such as a sclerosant or an adhesive is injected via an injection port 65, and the fluid is released through outer sheath side holes 44 into a vein V. Further, as shown in FIG. 16B, the expansion portion 30 is moved. As a result, the fluid such as a sclerosant or adhesive can be made to act on an inner wall surface of the vein V contacted and damaged by the expansion portion 30, thereby bringing about inflammation, thrombus formation, or growth of smooth muscle cells in the blood vessel wall, and achieving effective treatment of the vein V.

At the time of contracting the expansion portion 30, the cap 66 is attached to the injection port 65, and the pushing portion 110 is pushed, whereby the distal-side inclined surface of the engaging portion 111 is made to contact an edge of the second through-hole 103, the engaging portion 111 is bent to the inner side and disengaged from the second through-hole 103, and the engaging portion 111 is moved to the first through-hole 102 while compressing the coil spring 80. Upon arrival of the engaging portion 111 in the first through-hole 102, the engaging portion 111 is caught on the edge of the first through-hole 102, whereby a state with the expansion portion 30 in the contracted state is maintained. Thereafter, the medical device 90 can be withdrawn out of the vein V.

As described above, the medical device 90 according to the second embodiment includes: the operating portion main body 101 connected to the outer sheath 40 and formed with the first through-hole 102 (fitting recess); the pushing portion 110 capable of pushing (i.e., configured to push) the inner tube 20 distally; the engaging portion 111 connected to the pushing portion 110 and engageable with the first through-hole 102; and the pushing-out portion 104 pushing the engaging portion 111 fitted in the first through-hole 102 out of the first through-hole 102. In the initial state with the expansion portion 30 in the contracted state (i.e., the non-expanded position), the engaging portion 111 is in engagement with the first through-hole 102. When the engaging portion 111 in the initial state is disengaged from the first through-hole 102 by the pushing-out portion 104, the biasing force of the coil spring 80 (biasing member) causes the engaging portion 111 to move proximally, and the inner tube 20 is moved proximally relative to the outer sheath 40, whereby the expansion portion 30 is put into an expanded state. When the pushing portion 110 is pushed distally starting from the expanded state, the engaging portion 111 is fitted into the first through-hole 102, resulting in the initial state again. With such a configuration, it is possible to contract the expansion portion 30 by only pushing the pushing portion 110, and it is possible to expand the expansion portion 30 by only pushing in (i.e., inwardly in the radial direction) the pushing-out portion 104. Therefore, it is possible to easily switch between the expanded state and the contracted state of the expansion portion 30. Thus, enhanced operability is realized.

In a modification of the second embodiment, at least one other through-hole 105 may be formed between the first through-hole 102 and the second through-hole 103, as shown in FIG. 17. In addition, another pushing-out portion 106 is provided for pushing the engaging portion 111 in engagement with the other through-hole 105 out of the other through-hole 105. According to this configuration, it is possible to fix the expansion portion 30 in different sizes, as the engaging portion 111 is engaged with the other through-hole 105 or with the first through-hole 102. For this reason, a desirable size for the expansion portion 30 can be appropriately selected according to the conditions of a vein V to be treated.

Figure 18A:
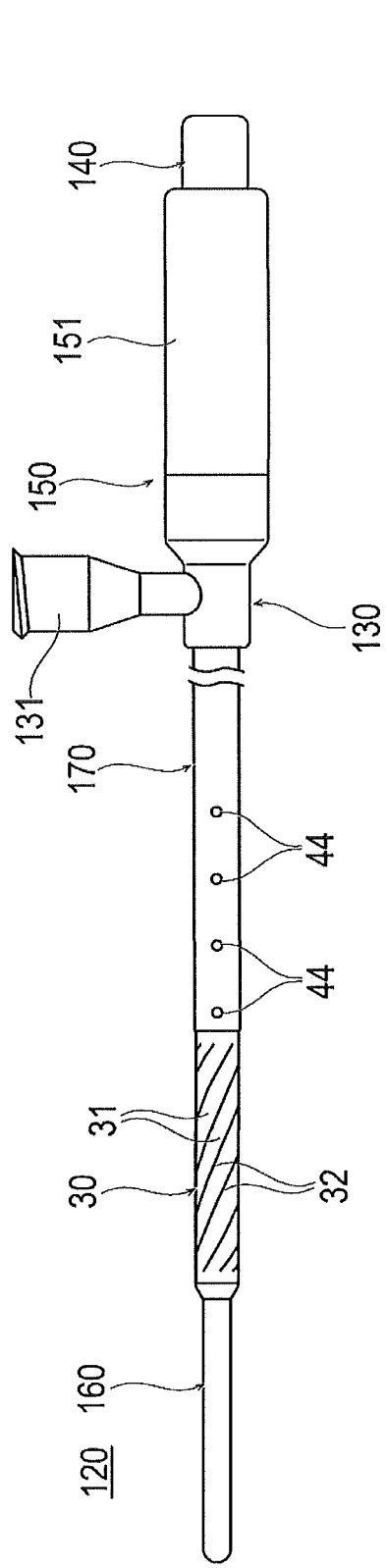
Figure 18B:
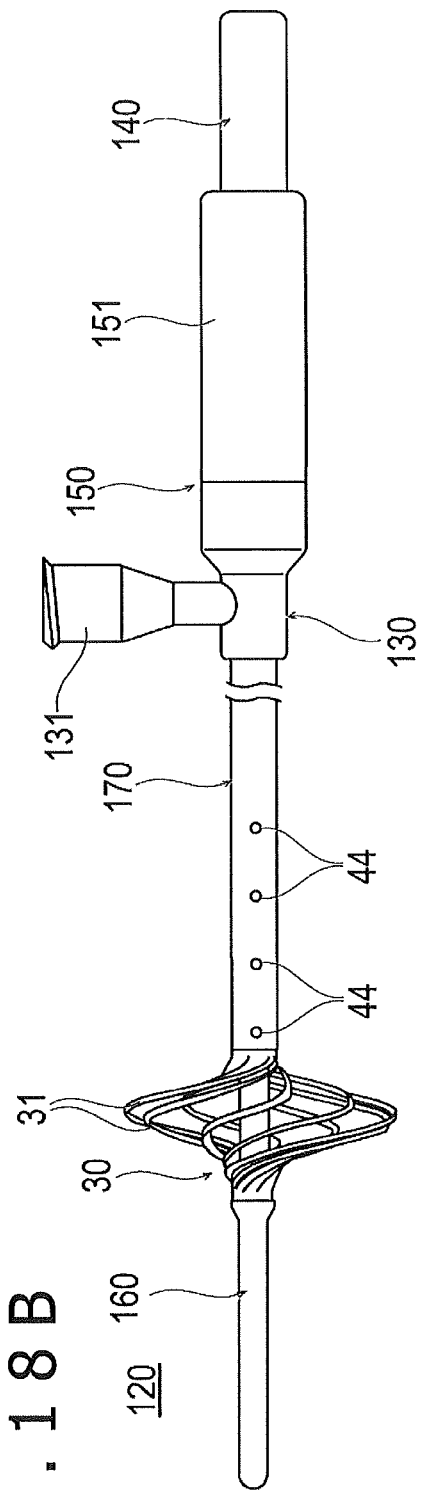

A medical device 120 according to a third embodiment, as shown in FIGS. 18A and 18B, differs from the first embodiment in that an injection port 131 is formed not at a pushing portion 140 but at a distal-side side portion of an operating portion 150. Note that the portions having the same or equivalent functions to those of the portions in the first embodiment above are denoted by the same reference symbols as used above, and descriptions of such portions will be omitted.

Figure 19:
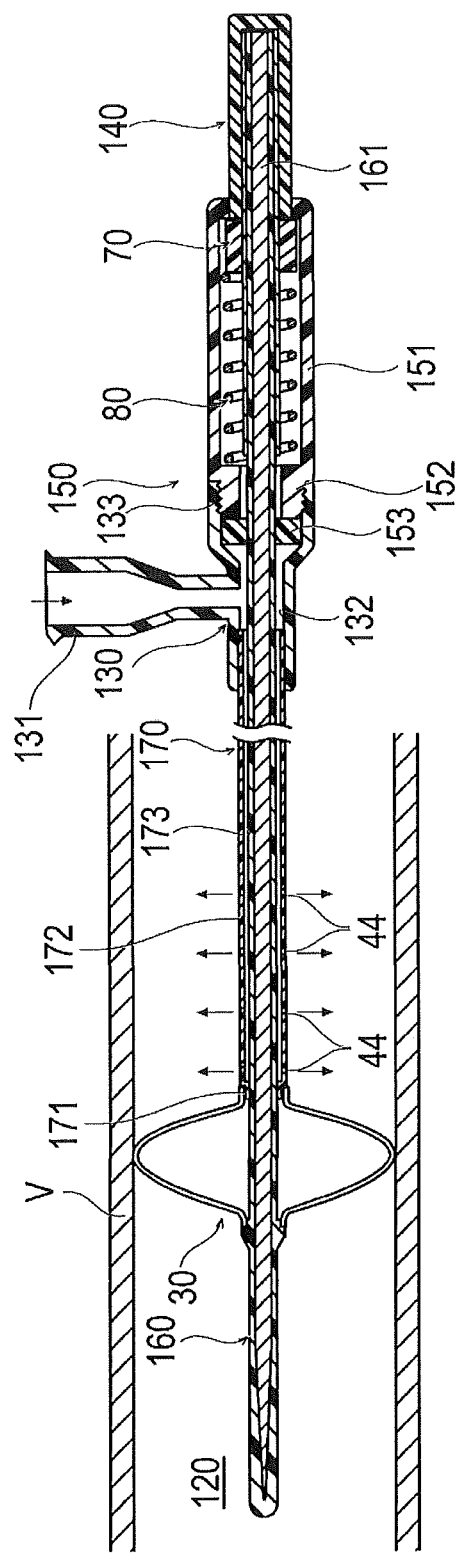
FIG. 19 is a schematic sectional view illustrating a manner in which fluid is released in a state in which the medical device according to the third embodiment is inserted in a vein.

An inner member 160 of the medical device 120 according to the third embodiment, as shown in FIG. 19, has an embedded core member 161 embedded, ranging to a proximal portion of the inner member 160 (i.e., the embedded core member 161 traverses from the distal end to the proximal end of the inner member 160).

An outer sheath 170 is a pipe shaped body (i.e., tubular) covering the inner member 160, and is axially movable relative to the inner member 160. A distal end portion 171 of the outer sheath 170 is slidable in close contact with an outer peripheral surface of the inner member 160. The outer sheath 170 possesses a distal end portion 171 and an outer sheath central portion 172 proximal of the distal end portion 171. The outer sheath central portion 172 possesses a greater inside diameter than the distal end portion 171 so that a predetermined gap is formed between the outer sheath central portion 172 and an outer peripheral surface of the inner member 160. The outer sheath central portion 172 is formed with a plurality of outer sheath side holes 44 which pierce from an inner surface to an outer surface of the outer sheath central portion 172 (i.e., through the wall of the outer sheath) and which are aligned in the axial direction. A lumen 173 is formed between the outer sheath 170 and the inner member 160 through which fluid such as a sclerosant or an adhesive can flow. The fluid having flowed into the lumen 173 can flow out to the exterior via the outer sheath side holes 44.

The operating portion 150, as shown in FIGS. 18A, 18B and 19, includes: an injection portion 130 to which a proximal portion of the outer sheath 170 is connected; an operating portion main body 151; the pushing portion 140 capable of axial movement relative to the operating portion main body 151; a rotatable body 70 rotatable within the operating portion main body 151; and a coil spring 80 (biasing member) disposed inside the operating portion main body 151.

The pushing portion 140 is a portion for an operator to perform a pushing operation. The pushing portion 140 is biased proximally by the coil spring 80 disposed inside the operating portion main body 151, and protrudes proximally from the operating portion main body 151. Note that the operating portion main body 151, the rotatable body 70, and the pushing portion 140 are provided with a knocking mechanism equivalent to that in the first embodiment.

The injection portion 130 is formed with the injection port 131 extending in a direction intersecting the axial direction of the medical device 120. The injection port 131 communicates with the lumen 173 of the outer sheath 170 by way of a passage 132 inside the injection portion 130. On the proximal side of the injection portion 130, there is formed a female screw portion 133 capable of screw engagement with a male screw portion 152 formed on the distal side of the operating portion main body 151.

On the inner side of the female screw portion 133 of the injection portion 130, there is a ring-shaped sealing member 153 which is elastically deformable. When the male screw portion 152 is screwed into the female screw portion 133, the sealing member 153 is compressed by the male screw portion 152 to be reduced in inside diameter, so that the sealing portion 153 is put into slidable close contact with an outer peripheral surface of the inner member 160. As a result, the fluid having flowed into the inside of the injection portion 130 can be inhibited from flowing into a region in which the knocking mechanism is provided, inside of the operating portion main body 151.

An operation of the medical device 120 according to the third embodiment will be described below.

The medical device 120 according to the third embodiment has a configuration in which the injection portion 130 provided on the distal side of the operating portion 150 is formed with the injection port 131. At the time of injecting fluid such as a sclerosant or an adhesive, a syringe or the like is connected to the injection port 131 (which is provided not at the pushing portion 140 but at the injection portion 130) from a side (i.e., orthogonal to the axial direction of the medical device 120). The fluid supplied through the injection port 131 passes through the passage 132 in the injection portion 130 to flow into the lumen 173 of the outer sheath 170, and is released via the outer sheath side holes 44 into a vein V. Note that since the configuration of the knocking mechanism is the same as in the first embodiment, the operations concerning the expansion and contraction of the expansion portion 30 are the same as in the first embodiment, and the description of such operations is omitted here.

Thus, in the medical device 120 according to the third embodiment, the injection port 131 is formed not at the pushing portion 140 but at the injection portion 130 provided on the distal side of the operating portion 150. For this reason, it is unnecessary for a syringe or the like containing fluid such as a sclerosant or an adhesive to be attached to and detached from the pushing portion 140 which is pushed and axially moved relative to the operating portion main body 151. Consequently, operations on the operating portion 150 are facilitated, and operability is enhanced.

A medical device 180 according to a fourth embodiment, as shown in FIGS. 20A and 20B, differs from the second embodiment in that an injection port 131 is formed not at a pushing portion 200 but at a distal-side side portion of an operating portion 190. The portions having the same or equivalent functions as those of the portions in the first to third embodiments above are denoted by the same reference symbols as used above, and descriptions of such portions will be omitted.

Figure 21:
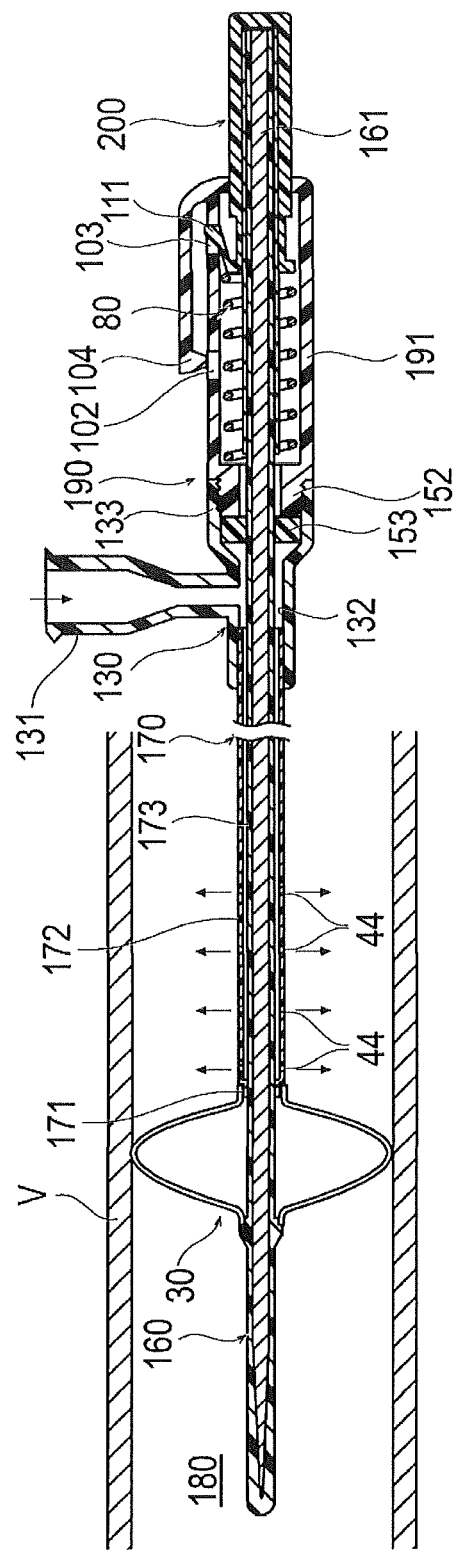
FIG. 21 is a schematic sectional view illustrating a manner in which fluid is released in a state in which the medical device according to the fourth embodiment is inserted in a vein.

An inner member 160 of the medical device 180 according to the fourth embodiment, as shown in FIG. 21, has an embedded core member 161 embedded, ranging to a proximal portion of the inner member 160 (i.e., the embedded core member 161 traverses from the distal end to the proximal end of the inner member 160).

An outer sheath 170 is a tube shaped body covering the inner member 160, and is axially movable relative to the inner member 160. A distal end portion 171 of the outer sheath 170 is slidable in close contact with an outer peripheral surface of the inner member 160. A lumen 173 is formed between the outer sheath 170 and the inner member 160, through which a sclerosant can flow. The sclerosant having flowed into the lumen 173 can be released to the exterior through outer sheath side holes 44.

The operating portion 190, as shown in FIGS. 20A, 20B and 21, includes: an injection portion 130 to which a proximal portion of the outer sheath 170 is connected; an operating portion main body 191; the pushing portion 200 axially movable relative to the operating portion main body 191; a pushing-out portion 104; and a coil spring 80 (biasing member) disposed inside the operating portion main body 191.

The pushing portion 200 is a portion for an operator to perform a pushing operation. The pushing portion 200 is biased proximally by the coil spring 80 disposed inside the operating portion main body 191, and protrudes proximally from the operating portion main body 191. Note that the operating portion main body 191, the pushing portion 200 and the pushing-out portion 104 are provided with a knocking mechanism equivalent to that in the second embodiment.

The injection portion 130 is formed with the injection port 131 extending in a direction intersecting the axial direction of the medical device 180. The injection port 131 communicates with the lumen 173 of the outer sheath 170 by way of a passage 132 formed inside the injection portion 130. On the proximal side of the injection portion 130, there is formed a female screw portion 133 capable of screw engagement with a male screw portion 152 which is formed on the distal side of the operating portion main body 191.

A ring-shaped sealing member 153 which is elastically deformable is disposed at the female screw portion 133 of the injection portion 130. When the male screw portion 152 is screwed into the female screw portion 133, the sealing member 153 is compressed by the male screw portion 152 to be reduced in inside diameter, resulting in that the sealing member 153 is put into sliding close contact with an outer peripheral surface of the inner member 160. This structure allows the fluid having flowed into the inside of the injection portion 130 to be prevented from flowing into a region where the knocking mechanism is provided, inside the operating portion main body 191.

An operation of the medical device 180 according to the fourth embodiment will be described below.

In the medical device 180 according to the fourth embodiment, the injection portion 130 provided on the distal side of the operating portion 190 is formed with the injection port 131. At the time of injecting fluid such as a sclerosant or an adhesive, a syringe or the like is connected to the injection port 131 (which is provided not at the pushing portion 200 but at the injection portion 130) from a side (i.e., orthogonal to the axial direction). The fluid supplied through the injection port 131 flows through the passage 132 in the injection portion 130 into the lumen 173 of the outer sheath 170, and is released into a vein V through the outer sheath side holes 44. Note that since the configuration of the knocking mechanism is the same as in the second embodiment, operations concerning the expansion and contraction of the expansion portion 30 are the same as in the second embodiment, and the description of such operations is omitted here.

Thus, in the medical device 180 according to the fourth embodiment, the injection port 131 is formed not at the pushing portion 200 but at the injection portion 130 provided on the distal side of the operating portion 190. For this reason, it is unnecessary for the syringe or the like containing the fluid such as a sclerosant or an adhesive to be connected to the pushing portion 200 which is pushed and axially moved relative to the operating portion main body 191. Consequently, operations on the operating portion 190 are facilitated, and operability is enhanced.

The present disclosure is not to be limited to the aforementioned embodiments, and various modifications can be made by one skilled in the art. For instance, while the fluid is released at a position proximal of the expansion portion 30 in the medical devices according to the aforementioned first to fourth embodiments, the fluid may be released at a position directly under the expansion portion 30 or at a position distal of the expansion portion 30. In such a configuration, after the expansion portion 30 in the expanded state is moved proximally to damage the blood vessel wall, the fluid is released from a portion distal of the expansion portion 30 (which is located inside the damaged portion of the blood vessel).

In addition, the configuration of the expansion portion is not specifically restricted so long as the expansion portion is radially expandable by moving the inner tube relative to the outer sheath.

The vein V is damaged by pulling the medical device 10 with the expansion portion 30 proximally in the medical devices according to the aforementioned first to fourth embodiments, but the vein V may also be damaged by pushing the medical device 10 with the expansion portion 30 distally.

Further, the inner tube and/or the outer sheath may be at least partially composed of porous material. In this case, the inner tube side holes and/or the outer sheath side holes may be pores of the porous material.

The detailed description above describes a medical device and a treatment method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device comprising:
an elongated outer sheath possessing a distal end;

an inner member inside of the outer sheath, the inner member protruding distally beyond the distal end of the outer sheath and possessing a distal end, and the inner member axially movable relative to the outer sheath, the inner member comprising a lumen and an outer surface;

an expansion portion positioned between the distal end of the outer sheath and the distal end of the inner member, the expansion portion being directly fixed to the distal end of the outer sheath and to the outer surface of the inner member, the expansion portion having a plurality of linear material portions extending along an axial direction of the inner member, the expansion portion being expandable in a radial direction of the inner member into an expanded state by moving the inner member proximally relative to the outer sheath, the expanded state being a maximum expansion state of the expansion portion such that the plurality of linear material portions extend farther radially outward in the expanded state than any other expansion positions of the expansion portion;

a biasing member biasing the inner member proximally relative to the outer sheath, and the biasing member being configured to compress when the inner member is moved distally relative to the outer sheath and to expand when the inner member is moved proximally relative to the outer sheath;

a fixing portion configured to fix a position of the inner member relative to a position of the outer sheath in a fixed state, the expansion portion being expanded into the expanded state when the inner member and the outer sheath are in the fixed state; and the fixing portion being configured to release from the fixed state when the fixing portion is pushed in a distal direction.

2. The medical device according to claim 1, wherein when the expansion portion is in the expanded state, the fixing portion stops proximal movement of the inner member relative to the outer sheath and permits the inner member to move distally relative to the outer sheath by contraction of the expansion portion to deform the biasing member.

3. The medical device according to claim 1, wherein
the outer sheath comprises a lumen permitting flow of a fluid and an outer wall comprising holes positioned to release the fluid out of the lumen of the outer sheath, and
the outer wall of the inner member comprises holes positioned to release the fluid out of the lumen of the inner member, the fluid entering the lumen of the outer sheath after being released from the lumen of the inner member.

4. The medical device according to claim 1, wherein the fixing portion is configured to fix the expansion portion in a plurality of sizes.

5. The medical device according to claim 1, wherein
the fixing portion comprises a cam main body connected to the outer sheath, a pushing portion configured to push the inner member distally, and a rotatable body configured to rotate within the cam main body;
the rotatable body possesses an outer peripheral surface and comprising an engaging projection projecting from the outer peripheral surface;
the cam main body is a tubular member possessing an inner wall surface and a distal end surface, the cam main body comprising a cam groove on the inner wall surface extending in an axial direction and a fitting recess configured to fit with the engaging projection of the rotatable body, and the distal end surface of the cam main body having an inclined surface configured to contact the engaging projection and rotate the engaging projection in a circumferential direction;
the pushing portion comprises a plurality of projections and a plurality of recesses aligned in the circumferential direction at a distal end of the pushing portion;
the engaging projection is fitted within the fitting recess in an initial state in which the expansion portion is contracted;
the pushing portion is configured to move distally in the initial state to cause one of the plurality of projections to contact and move the engaging projection distally and disengage the engaging projection from the fitting recess, a biasing force of the biasing member causing the engaging projection to slide along the inclined surface to align with the cam groove while the rotatable body correspondingly rotates, the pushing portion being in a disengaged state;
when the pushing portion is released from the disengaged state, the engaging projection is configured to move proximally along the cam groove causing the inner member to move proximally relative to the outer sheath so that the expansion portion expands into the expanded state; and
the pushing portion is configured to move distally when the expansion portion is in the expanded state to cause one of the plurality of projections to move the engaging projection distally and disengage the engaging projection from the cam groove, the biasing force of the biasing member causing the engaging projection to slide along the inclined surface to be guided into the fitting recess while the rotatable body correspondingly rotates.

6. The medical device according to claim 1,
wherein the fixing portion comprises:
an operating portion main body connected to the outer sheath, the operating portion main body possessing an inner surface and comprising a fitting recess in the inner surface,
a pushing portion configured to move the inner member distally, the pushing portion being coaxial with the inner member and moving distally together with the inner member,
an engaging portion connected to the pushing portion and configured to fit within and engage with the fitting recess, and
a pushing-out portion adapted to push the engaging portion fitted within and engaging with the fitting recess out of the fitting recess;
the engaging portion configured to engage with the fitting recess in an initial state in which the expansion portion is contracted;
the engaging portion configured to disengage from the fitting recess when the pushing-out portion is proximally pushed in the initial state to cause the engaging portion to be moved proximally by the biasing force of the biasing member, the inner member configured to move proximally relative to the outer sheath so that the expansion portion comes into an expanded state; and
the pushing portion is configured to move distally from the expanded state to cause the engaging portion to fit into the fitting recess, resulting in the initial state.

7. A medical device comprising:
an elongated outer sheath possessing a distal end, the elongated outer sheath comprising a lumen, an outer sheath wall and holes penetrating through the outer sheath wall, the lumen of the outer sheath permitting flow of a fluid;

an inner member inside the outer sheath, the inner member possessing a distal end positioned distally of the distal end of the outer sheath, and the inner member being axially movable in an axial direction relative to the outer sheath, the inner member comprising a lumen an inner member wall, and holes penetrating through the inner member wall, the lumen of the inner member permitting flow of the fluid;

an expansion portion between the distal end of the outer sheath and the distal end of the inner member, the expansion portion comprising a plurality of linear material portions, the expansion portion being movable between a non-expanded position in which the linear material portions extend in the axial direction and an expanded position in which the linear material portions expand radially outwardly by virtue of the inner member moving proximally in a proximal direction relative to the outer sheath;

a rotatable member rotatably positioned inside the outer sheath;

a body connected to the outer sheath;

a biasing member applying a biasing force to the rotatable member in the proximal direction so that the rotatable member is a spring-biased rotatable member;

the rotatable member being rotatable between a first position in which the body prevents the biasing force from axially moving the inner member in the proximal direction, whereby the expansion portion remains in the non-expanded position, and a second position in which the spring-biased rotatable member applies the biasing force to the inner member to automatically axially move the inner member relative to the outer sheath in the proximal direction, whereby the expansion portion expands to the expanded position;

the inner member and the outer sheath being relatively axially movable so that the inner member moves in a distal direction to cause a part movable with the inner member to contact the rotatable member so that the rotatable member shifts from the first position to the second position, whereupon the biasing force of the biasing member is applied to the inner member to axially move the inner member in the proximal direction;

the holes in the inner member wall are positioned so that the fluid flows from the lumen of the inner member into the lumen of the outer sheath;

the holes in the outer sheath wall are positioned so that the fluid flows from the lumen of the outer sheath to outside of the medical device; and the holes in the inner member wall and the holes in the outer sheath wall are misaligned in a circumferential direction when the expansion portion is in the expansion state.

8. The medical device according to claim 7, wherein when the expansion portion is in the expanded state, the body prevents the proximal movement of the inner member relative to the outer sheath and permits the inner member to move distally relative to the outer sheath by contraction of the expansion portion to deform the biasing member.

9. The medical device according to claim 7, wherein the holes in the inner member wall are between the holes in the outer sheath wall in the axial direction when the expansion portion is in the expansion state.

10. The medical device according to claim 7, further comprising a rigid member embedded in the inner member, the rigid member located distally of the expansion portion in the non-expanded position.

11. The medical device according to claim 10, wherein the rigid member possesses a proximal end, the proximal end of the rigid member configured to move proximally of a distal end of the expansion portion when the expansion portion is in the expanded position.

12. A medical device comprising:

an elongated outer sheath possessing a distal end;

an inner member inside of the outer sheath, the inner member comprising a distal end, the inner member protruding distally beyond the distal end of the outer sheath such that an outer diameter of the medical device at the distal end of the inner member is smaller than the outer diameter of the medical device at the distal end of the outer sheath, the inner member being axially movable relative to the outer sheath, the inner member comprising a lumen permitting flow of a fluid and an outer surface;

an expansion portion positioned between the distal end of the outer sheath and the distal end of the inner member, the expansion portion being directly fixed to the distal end of the outer sheath and the outer surface of the inner member, the expansion portion having a plurality of linear material portions extending along an axial direction of the inner member, the expansion portion being expandable in a radial direction of the inner member into an expanded state by moving the inner member proximally relative to the outer sheath, the expanded state being a maximum expansion state of the expansion portion such that the plurality of linear material portions extend farther radially outward in the expanded state than any other expansion positions of the expansion portion;

a biasing member biasing the inner member proximally relative to the outer sheath, and the biasing member being configured to compress when the inner member is moved distally relative to the outer sheath and to expand when the inner member is moved proximally relative to the outer sheath;

a fixing portion configured to fix a position of the inner member relative to a position of the outer sheath in a fixed state, the expansion portion being expanded into the expanded state when the inner member and the outer sheath are in the fixed state;

the fixing portion being configured to release the expansion portion from the fixed state when the fixing portion is pushed in a distal direction;

the fixing portion comprising a cam main body connected to the outer sheath, a pushing portion configured to push the inner member distally, and a rotatable body configured to rotate within the cam main body, the biasing member being within the cam main body;

the rotatable body comprises an outer peripheral surface and a plurality of engaging projections projecting from the outer peripheral surface, the plurality of engaging projections being spaced apart along the outer peripheral surface of the rotatable body to define a plurality of recesses between the plurality of engaging projections;

the pushing portion comprising a plurality of projections and a plurality of recesses aligned in the circumferential direction at a distal end of the pushing portion;

the projections of the pushing portion being fitted within the recesses of the rotatable body in an initial state in which the expansion portion is contracted;

the projections of the pushing portion being proximal to and outside of the recesses of the rotatable body in the expanded state when the expansion portion is contracted; and the projections of the pushing portion and the engaging projections of the rotatable body each comprising inclined end surfaces.

* * * * *